US011577212B2

(12) United States Patent
Surwade et al.

(10) Patent No.: US 11,577,212 B2
(45) Date of Patent: Feb. 14, 2023

(54) STIMULI-RESPONSIVE MICRO-RESERVOIRS FOR RELEASE OF ENCAPSULANTS

(71) Applicant: SAS Nanotechnologies LLC, Newark, DE (US)

(72) Inventors: Sumedh Surwade, Newark, DE (US); Kalpana Madgula, Newark, DE (US)

(73) Assignee: SAS Nanotechnologies Inc., Wilmington, DE (US)

( * ) Notice: Subject to any disclaimer, the term of this patent is extended or adjusted under 35 U.S.C. 154(b) by 177 days.

(21) Appl. No.: 16/513,220

(22) Filed: Jul. 16, 2019

(65) Prior Publication Data

US 2020/0016564 A1 Jan. 16, 2020

Related U.S. Application Data

(60) Provisional application No. 62/698,686, filed on Jul. 16, 2018, provisional application No. 62/862,910, filed on Jun. 18, 2019.

(51) Int. Cl.
*B01J 13/18* (2006.01)
*C09D 5/08* (2006.01)
(Continued)

(52) U.S. Cl.
CPC .............. *B01J 13/18* (2013.01); *A01N 25/28* (2013.01); *A01N 43/80* (2013.01); *A01N 43/90* (2013.01);
(Continued)

(58) Field of Classification Search
CPC ........ A01N 25/28; A01N 43/80; A01N 43/90; A01N 51/00; A61K 9/5031; A61K 31/635;
(Continued)

(56) References Cited

U.S. PATENT DOCUMENTS 6,365,066 B1  4/2002  Podszun et al.
6,527,849 B2  3/2003  Dry
(Continued)

FOREIGN PATENT DOCUMENTS

CN  101259403 B  6/2010
EP  0758633 A1  2/1997
(Continued)

OTHER PUBLICATIONS

Pirhady Tavandashti, N., Ghorbani, M., Shojaei, A., Mol, J.M.C., Terryn, H., Baert, K., Gonzalez-Garcia, Y., "Inhibitor-loaded conducting polymer capsules for active corrosion protection of coating defects", Corrosion Science, 2016, 112, 138-149 (Year: 2016).*

(Continued)

*Primary Examiner* — James C Goloboy
(74) *Attorney, Agent, or Firm* — BakerHostetler

(57) ABSTRACT

This invention relates to polymer-based partially-open, hollow reservoirs in the nano-size to micro-size range that encapsulate an additive, which can be released from the reservoirs using specific event stimuli such as reduction-oxidation and voltage change, or at will, using the same stimuli. This invention also relates to method preparing such reservoirs, and for releasing the additive. This invention further relates to matrix that comprises such reservoirs and the method of preparing such matrix. This invention also relates to applications, for example in corrosion inhibition, lubrication, and adhesion, that benefit from using such a controlled release of an additive.

27 Claims, 13 Drawing Sheets

(51) Int. Cl.

| | |
|---|---|
| C09J 11/08 | (2006.01) |
| C09J 11/06 | (2006.01) |
| C05C 9/00 | (2006.01) |
| C09B 67/08 | (2006.01) |
| C09B 11/08 | (2006.01) |
| A61K 9/50 | (2006.01) |
| A01N 25/28 | (2006.01) |
| A01N 43/80 | (2006.01) |
| A01N 43/90 | (2006.01) |
| C08G 73/02 | (2006.01) |
| A61K 33/38 | (2006.01) |
| A61K 31/635 | (2006.01) |
| G01N 31/22 | (2006.01) |
| B01J 13/20 | (2006.01) |
| C05G 5/30 | (2020.01) |
| A01N 51/00 | (2006.01) |
| C09D 5/00 | (2006.01) |
| C10N 30/06 | (2006.01) |
| C10N 30/10 | (2006.01) |
| C10N 30/12 | (2006.01) |
| C10N 50/00 | (2006.01) |
| C08K 9/10 | (2006.01) |

(52) U.S. Cl.
CPC ............ *A01N 51/00* (2013.01); *A61K 9/5031* (2013.01); *A61K 31/635* (2013.01); *A61K 33/38* (2013.01); *B01J 13/20* (2013.01); *C05C 9/00* (2013.01); *C05G 5/37* (2020.02); *C08G 73/026* (2013.01); *C08G 73/0266* (2013.01); *C09B 11/08* (2013.01); *C09B 67/0013* (2013.01); *C09D 5/00* (2013.01); *C09D 5/082* (2013.01); *C09J 11/06* (2013.01); *C09J 11/08* (2013.01); *G01N 31/22* (2013.01); *C08K 9/10* (2013.01); *C10M 2201/084* (2013.01); *C10M 2215/26* (2013.01); *C10M 2217/046* (2013.01); *C10M 2219/066* (2013.01); *C10M 2223/00* (2013.01); *C10M 2223/045* (2013.01); *C10N 2030/06* (2013.01); *C10N 2030/10* (2013.01); *C10N 2030/12* (2013.01); *C10N 2050/12* (2020.05)

(58) Field of Classification Search
CPC ........... A61K 33/38; B01J 13/18; B01J 13/20; C05C 9/00; C08K 9/10; C09B 11/08; C09B 67/0013; C09B 67/0097; C09D 5/00; C09D 5/08; C09D 5/082; C09D 5/16; C09D 5/1606; C09D 7/40; C09D 7/61; C09D 7/63; C09J 11/06; C09J 11/08; C10M 125/22; C10M 133/12; C10M 137/10; C10M 149/22; C10M 161/00; C10M 171/06; C10M 2201/084; C10M 2207/026; C10M 2207/027; C10M 2207/125; C10M 2207/144; C10M 2207/16; C10M 2215/064; C10M 2215/065; C10M 2215/08; C10M 2215/26; C10M 2217/046; C10M 2219/04; C10M 2219/066; C10M 2219/088; C10M 2223/00; C10M 2223/045; C10N 2020/06; C10N 2030/06; C10N 2030/10; C10N 2030/12; C10N 2050/12; G01B 31/22
See application file for complete search history.

(56) References Cited

U.S. PATENT DOCUMENTS

| | | | |
|---|---|---|---|
| 9,340,676 B2 | 5/2016 | Shchukin et al. | |
| 10,364,359 B2 | 7/2019 | Virtanen | |
| 2008/0305362 A1* | 12/2008 | Schroeder | B60J 5/0405 428/697 |
| 2009/0136816 A1 | 5/2009 | Kang et al. | |
| 2017/0073610 A1* | 3/2017 | Hsu | C11D 17/0039 |

FOREIGN PATENT DOCUMENTS

| | | |
|---|---|---|
| EP | 1108824 A1 | 6/2001 |
| KR | 2011-0017780 A | 2/2011 |
| KR | 10-1753626 B1 | 7/2017 |
| KR | 2017-0096993 A | 8/2017 |
| WO | 2018055102 A1 | 3/2018 |

OTHER PUBLICATIONS

H. Sun, X. Shen, L. Yao, S. Xing, H. Wang, Y. Feng, H. Chem, "Measuring the Unusually Slow Ionic Diffusion in Polyaniline via Study of Yolk-Shell Nanostructures", J. Am Chem. Soc., 2012, 134, 27, 11243-11250 (Year: 2012).*

Ahn, K. J.; Lee, Y.; Choi, H.; Kim, M. S.; Im, K.; Noh, S.; Yoon, H.: Surfactant-Templated Synthesis of Polypyrrole Nanocages as Redox Mediators for Efficient Energy Storage. Scientific Reports 2015, 5.

Anilkumar, P.; Jayakannan, M.: Divergent Nanostructures from Identical Ingredients: Unique Amphiphilic Micelle Template for Polyaniline Nanofibers, Tubes, Rods, and Spheres. Macromolecules 2008, 41, 7706-7715.

Tran, H. D.; Li, D.; Kaner, R. B.: One-Dimensional Conducting Polymer Nanostructures: Bulk Synthesis and Applications. Advanced Materials 2009, 21, 1487-1499.

Chen, F.; Liu, P.: Conducting Polyaniline Nanoparticles and Their Dispersion for Waterborne Corrosion Protection Coatings. Acs Applied Materials Interfaces 2011, 3, 2694-2702.

Fang, J.; Xu, K.; Zhu, L. H.; Zhou, Z. X.; Tang, H. Q.: A study on mechanism of corrosion protection of polyaniline coating and its failure. Corrosion Science 2007, 49, 4232-4242.

Han, J.; Song, G. P.; Guo, R.: A facile solution route for polymeric hollow spheres with controllable size. Advanced Materials 2006, 18, 3140-3144.

Han, J.; Song, G. P.; Guo, R.: Synthesis of polymer hollow spheres with holes in their surfaces. Chemistry of Materials 2007, 19, 973-975.

Anticorrosion Coatings Market Revenue, 2015-2021; Industry ARC, htttp://industryarc.com/Report/11671/anticorrosion-coatings-market. html: Website, Retrieved from Internet on Oct. 22, 2019, 8 pages.

Markets and Markets; Publisher Sample; Anti-Corrosion Coating Market-Global Trends & Forecasts to 2019; htttp://marketsandmarkets.com/Market-Reports/anti-corrosion-coating-market-155215822. html: Website; 16 pages.

China's Anti-Corrosion Coatings Market; PCI Paint & Coatings Industry, htttp://pcimag.com/articles/99921-chinas-anti-corrosion-coatings-market: Website, Retrieved from Internet on Oct. 22, 2019, 6 pages.

Explore the World of Piping; Effects & Economic Impact of Corrosion; Materials—Corrosion and Corrosion Allowance ; htttp://wermac.org/materials/corrosion.html: Website. Retrieved from Internet on Jan. 7, 2020; 6 pages.

Coatings, High-Performance Anticorrosion; Specialty Chemicals Update Program; htttps://ihs.com/products/chemical-high-performance-anticorrosion-scup; Published May 2019; Retrieved from Internet on Oct. 22, 2019; 8 pages.

Jin, E.; Liu, N.; Lu, X. F.; Zhang, W. J.: Novel micro/nanostructures of polyaniline in the presence of different amino acids via a self-assembly process. Chemistry Letters 2007, 36, 1288-1289.

Kolla, H. S.; Surwade, S. P.; Zhang, X. Y.; MacDiarmid, A. G.; Manohar, S. K.: Absolute molecular weight of polyaniline. Journal of the American Chemical Society 2005, 127, 16770-16771.

(56) References Cited

OTHER PUBLICATIONS

Kowalski, D.; Ueda, M.; Ohtsuka, T.: Self-healing ion-permselective conducting polymer coating. Journal of Materials Chemistry 2010, 20, 7630-7633.
Kumar, A.; Stephenson, L. D.; Murray, J. N.: Self-healing coatings for steel. Progress in Organic Coatings 2006, 55, 244-253.
Laslau, C.; Zujovic, Z. D.; Zhang, L. J.; Bowmaker, G. A.; Travas-Sejdic, J.: Morphological Evolution of Self-Assembled Polyaniline Nanostuctures Obtained by pH-stat Chemical Oxidation. Chemistry of Materials 2009, 21, 954-962.
Li, G. C.; Zhang, C. Q.; Peng, H. R.; Chen, K. Z.; Zhang, Z. K.: Hollow Self-Doped Polyaniline Micro/Nanostructures: Microspheres, Aligned Pearls, and Nanotubes. Macromolecular Rapid Communications 2008, 29, 1954-1958.
Li, J. B.; Jia, Q. M.; Zhu, J. W.; Zheng, M. S.: Interfacial polymerization of morphologically modified polyaniline: from hollow microspheres to nanowires. Polymer International 2008, 57, 337-341.
Liu, P.; Zhang, L.: Hollow Nanostructured Polyaniline: Preparation, Properties and Applications. Critical Reviews in Solid State and Materials Sciences 2009, 34, 75-87.
Yu, et al.,; Full View of Single-Molecule Force Spectroscopy of Polyaniline in Oxidized, Reduced, and Doped States. Langmuir 2009, 25, 10002-10006.
Lv, L. P.; Zhao, Y.; Vilbrandt, N.; Gallei, M.; Vimalanandan, A.; Rohwerder, M.; Landfester, K.; Crespy, D.: Redox Responsive Release of Hydrophobic Self-Healing Agents from Polyaniline Capsules. Journal of the American Chemical Society 2013, 135, 14198-14205.
Montemor, M. F.: Functional and smart coatings for corrosion protection: A review of recent advances. Surface Coatings Technology 2014, 258, 17-37.
Quinet, M.; Neveu, B.; Moutarlier, V.; Audebert, P.; Ricq, L.: Corrosion protection of sol-gel coatings doped with an organic corrosion inhibitor: Chloranil. Progress in Organic Coatings 2007, 58, 46-53.
Radhakrishnan, S.; Sonawane, N.; Siju, C. R.: Epoxy powder coatings containing polyaniline for enhanced corrosion protection. Progress in Organic Coatings 2009, 64, 383-386.
Sairam, M.; Nataraj, S. K.; Aminabhavi, T. M.; Roy, S.; Madhusoodana, C. D.: Polyaniline membranes for separation and purification of gases, liquids, and electrolyte solutions. Separation and Purification Reviews 2006, 35, 249-283.
Vimalanandan, A.; Lv, L. P.; Tran, T. H.; Landfester, K.; Crespy, D.; Rohwerder, M.: Redox-Responsive Self-Healing for Corrosion Protection. Advanced Materials 2013, 25, 6980-6984.
Shchukin, D. G.: Container-based multifunctional self-healing polymer coatings. Polymer Chemistry 2013, 4, 4871-4877.
Sitaram, S. P.; Stoffer, J. O.; Okeefe, T. J.: Application of conducting polymers in corrosion protection. Journal of Coatings Technology 1997, 69, 65-69.
Sorensen, P. A.; Kiil, S.; Dam-Johansen, K.; Weinell, C. E.: Anticorrosive coatings: a review. Journal of Coatings Technology and Research 2009, 6, 135-176.
Sui, J.; Zhang, L. J.; Peng, H.; Travas-Sejdic, J.; Kilmartin, P. A.: Self-assembly of poly(o-methoxyaniline) hollow nanospheres from a polymeric acid solution. Nanotechnology 2009, 20-23.

Tavandashti, N. P.; Ghorbani, M.; Shojaei, A.; Mol, J. M. C.; Terryn, H.; Baert, K.; Gonzalez-Garcia, Y.: Inhibitor-loaded conducting polymer capsules for active corrosion protection of coating defects. Corrosion Science 2016, 112, 138-149.
Tian, Z. F.; Yu, H. J.; Wang, L.; Saleem, M.; Ren, F. J.; Ren, P. F.; Chen, Y. S.; Sun, R. L.; Sun, Y. B.; Huang, L.: Recent progress in the preparation of polyaniline nanostructures and their applications in anticorrosive coatings. Rsc Advances 2014, 4, 28195-28208.
Wang, J. G.; Torardi, C. C.; Duch, M. W.: Polyaniline-related ion-barrier anticorrosion coatings II. Protection behavior of polyaniline, cationic, and bipolar films. Synthetic Metals 2007, 157, 851-858.
Wang, J. P.; Zhang, D. H.: One-Dimensional Nanostructured Polyaniline: Syntheses, Morphology Controlling, Formation Mechanisms, New Features, and Applications. Advances in Polymer Technology 2013, 32, E323-E368.
Wei, H. G.; Wang, Y. R.; Guo, J.; Shen, N. Z.; Jiang, D. W.; Zhang, X.; Yan, X. R.; Zhu, J. H.; Wang, Q.; Shao, L.; Lin, H. F.; Wei, S. Y.; Guo, Z. H.: Advanced micro/nanocapsules for self-healing smart anticorrosion coatings. Journal of Materials Chemistry A 2015, 3, 469-480.
Wei, Z. X.; Wan, M. X.: Hollow microspheres of polyaniline synthesized with an aniline emulsion template. Advanced Materials 2002, 14, 1314-1317.
Wessling, B. Passivation of metals by coating with polyaniline—corrosion potential shift and morphological changes. Advanced Materials 1994, 6, 226-228.
Yang, Y.; Chu, Y.; Yang, F. Y.; Zhang, Y. P.: Uniform hollow conductive polymer microspheres synthesized with the sulfonated polystyrene template. Materials Chemistry and Physics 2005, 92, 164-171.
Zhang, L. J.; Peng, H.; Sui, J.; Soeller, C.; Kilmartin, P. A.; Travas-Sejdic, J.: Self-Assembly of Poly(o-methoxyaniline) Hollow Microspheres. Journal of Physical Chemistry C 2009, 113, 9128-9134.
Zhang, L. J.; Wan, M. X.: Self-assembly of polyaniline—From nanotubes to hollow microspheres. Advanced Functional Materials 2003, 13, 815-820.
Zhang, X. Y.; Goux, W. J.; Manohar, S. K.: Synthesis of polyaniline nanofibers by "nanofiber seeding". Journal of the American Chemical Society 2004, 126, 4502-4503.
Zhu, Y.; Ren, G. Q.; Wan, M. X.; Jiang, L.: 3D Hollow Microspheres Assembled from 1D Polyaniline Nanowires through a Cooperation Reaction. Macromolecular Chemistry and Physics 2009, 210, 2046-2051.
International Patent Application No. PCT/US2019/042030; Int'l Preliminary Report on Patentability; dated Jan. 28, 2021; 6 pages.
European Patent Application No. 19838786.2; Extended Search Report; dated Feb. 24, 2022; 11 pages.
Sun et al.; "Measuring the Unusually Slow Ionic Diffusion Study of Yolk-Shell Nanostructures"; Journal of the American Chemical Society; vol. 134; 2012; p. 11243-11250.
Han et al.; "Reactive Template Method to Synthesize Gold Nanoparticles with Controllable Size and Morphology Supported on Shells of Polymer Hollow Microspheres and Their Application for Aerobic Alcohol Oxidation in Water"; Advanced Functional Materials; vol. 19; 2009; p. 1112-1117.

* cited by examiner

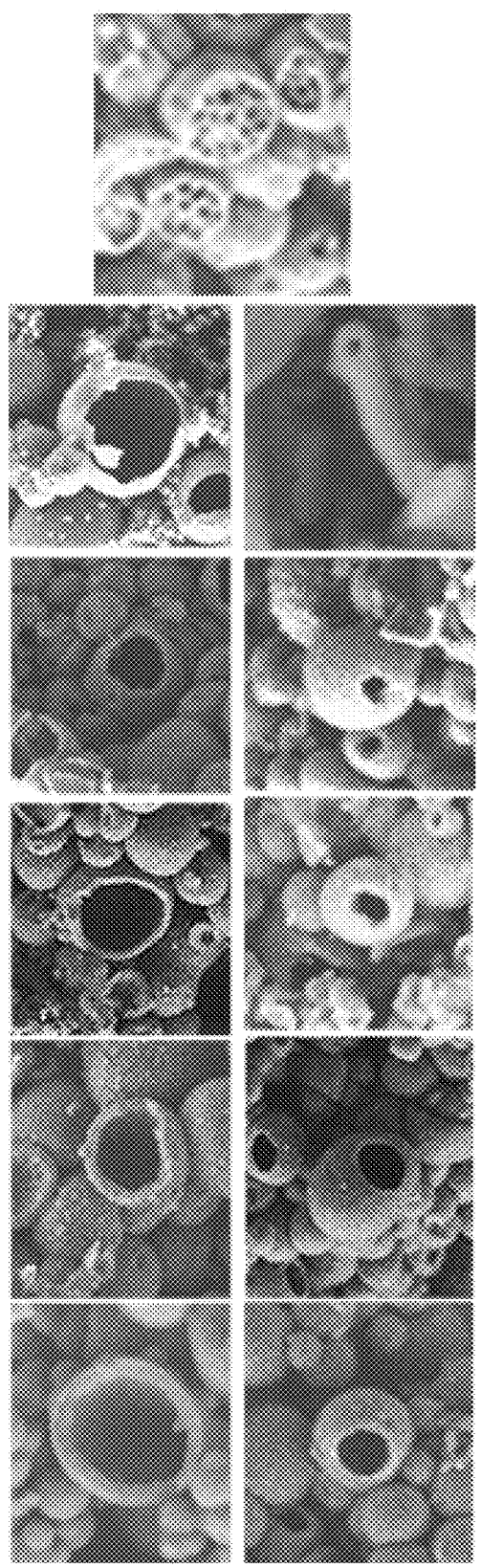
FIG. 1.1

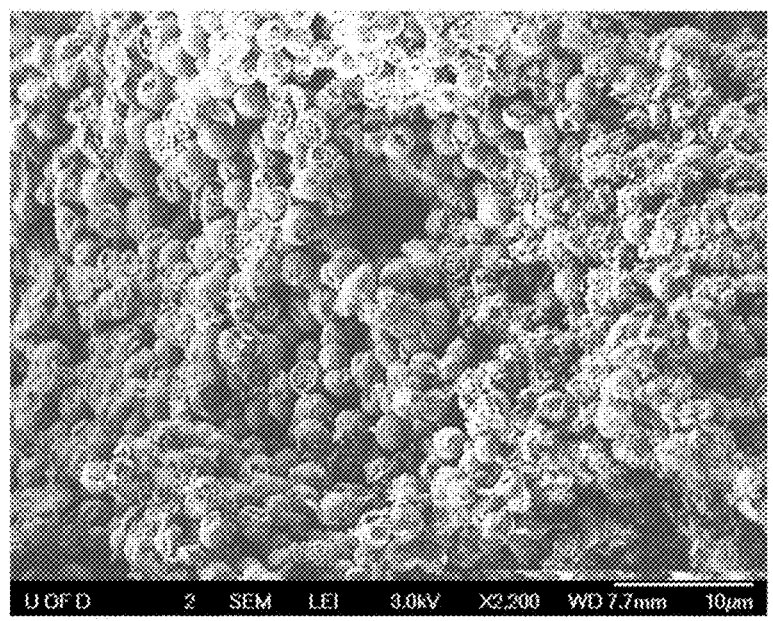
FIG. 1.2

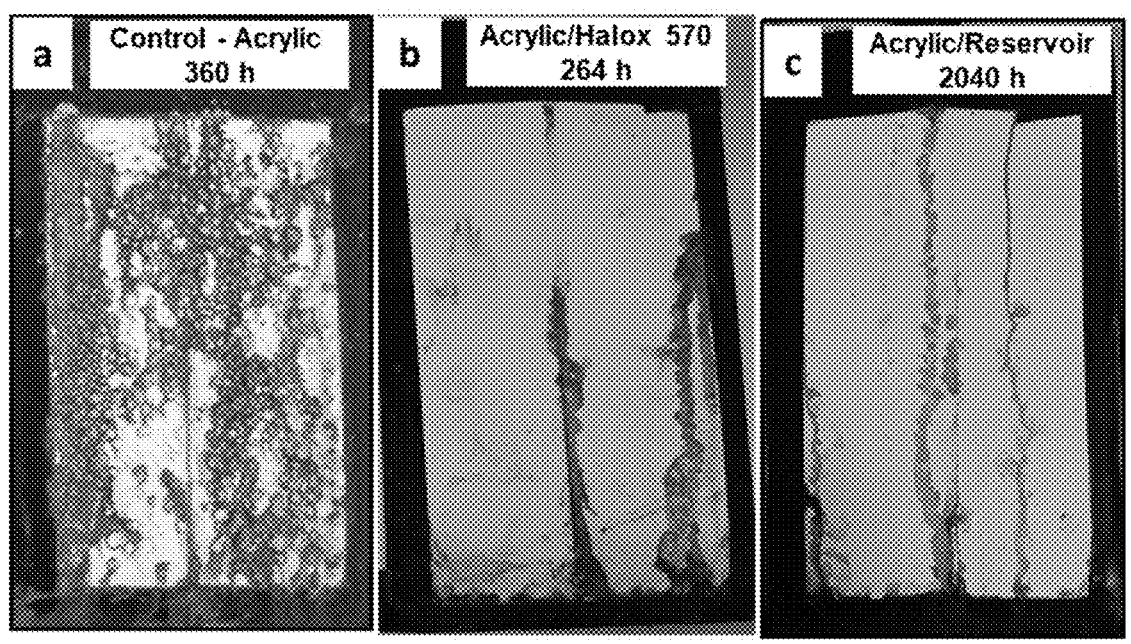
FIG. 9.1

STIMULI-RESPONSIVE MICRO-RESERVOIRS FOR RELEASE OF ENCAPSULANTS

CROSS REFERENCE TO RELATED APPLICATIONS

This application claims the benefit of U.S. Provisional Application No. 62/698,686, filed Jul. 16, 2018, and U.S. Provisional Application No. 62/862,910, filed Jun. 18, 2019, the entireties of which are incorporated herein for any and all purposes.

GOVERNMENT RIGHTS

This invention was made with Government support under grant #1746264 awarded by the National Science Foundation. The Government has certain rights to this invention.

TECHNICAL FIELD

This invention relates to polymer-based partially-open, hollow reservoirs in the nano-size to micro-size range that encapsulate an additive, which can be released from the reservoirs using specific event triggers such as reduction-oxidation and voltage change, or at will, using the same triggers. This invention also relates to method preparing such reservoirs, and for releasing the additive. This invention further relates to matrix that comprises such reservoirs and the method of preparing such matrix. This invention also relates to applications, for example in corrosion inhibition, lubrication, and adhesion, that benefit from using such a controlled release of an additive.

BACKGROUND

In one embodiment, the present invention relates to delivering a particular functional additive in the nano-size to micro-size scale to a specific site, and at a specific time, when required. This solution is an advantageous proposition to consumer applications and in the industry having such need. Given below are examples of such need in a few industries. This invention equally applies to other industries.

A. Corrosion Industry

Industries such as oil and gas, automotive, chemical plants, marine, and construction-infrastructure use metals abundantly. Corrosion of metals is one of the biggest problems in the industrial world. Corrosion incurs massive economic losses, inflicts severe environmental damage, and wastes significant resources associated with it. Corrosion often results in structural failure sometimes even leading to loss of human life. Protecting metals from corrosion renders efficient functioning and safety of these industries.

To prevent metal corrosion, coatings containing corrosion inhibiting additives are applied on the metal surface. The most effective anticorrosive coatings contain corrosion inhibiting additives of heavy metal origin: for example, chromium, zinc, lead, and their compounds. Health, safety, and environmental concerns mandate that the heavy metal based anticorrosion additives be replaced with less dangerous additives. Non-heavy metal based corrosion inhibitors, while initially effective, tend to leach out from the coating surface owing to rain and weather events, rendering the coating ineffective. Also, coatings degrade due to mechanical fatigue, or from scratches and dents due to wear, which exposes the underlying metal. The metal starts corroding immediately, making the corrosion inhibitor in anticorrosive coating ineffective.

Therefore, to improve the corrosion-inhibition longevity of the coating, the corrosion inhibitor in it should be preserved for a longer time. Longevity also improves if the corrosion inhibitor is availed to arrest corrosion immediately when a scratch or mechanical damage occurs on the metal surface. Encapsulating corrosion the inhibitor in reservoirs or capsules preserve them in the coatings for a longer time, as provided in the present invention.

B. Lubricant Industry

Lubricants are used in applications that typically involve moving metal parts. They reduce the friction generated between moving parts due to wear and heating, for example. Because lubricants also coat metal parts, they help inhibit corrosion. Functional additives are added into lubricants to increase the performance. For example, a lubricant may include antioxidant additives that prevent the oil from thickening; friction modifier additives that increase engine efficiency; dispersant additives that hold contaminants in suspension; antifoam additives that inhibit the production and retention of air bubbles; detergent additives that reduce deposits on metal; and corrosion inhibiting additives to inhibit corrosion of metals.

Changing lubricant often is expensive and disposal of used lubricant contributes towards soil, and ground water contamination if not properly managed. Therefore, to increase the lubricant's life and consequently the time interval between change of lubricant, it is important to preserve the additives in lubricants for a longer time.

Encapsulating additives in reservoirs preserves them in the lubricant for a longer time, as provided in the present invention.

C. Adhesive Industry

In electronic devices, conductive elements may be bonded to one another by means of adhesives. Manufacturers of metal components use structural adhesives to replace conventional fastening techniques such as rivets, bolts, and welding. Adhesives offer many attractive properties that include improved product performance, aesthetics, reduced overall assembly time, and lower production costs. Additionally, adhesives preclude much of the stress point concentration, corrosion, and component damage often seen with rivets, bolts, welding, and other traditional fastening methods.

There is also considerable interest in attaching two different types of materials together, e.g. in automotive applications, to reduce the overall weight of the structure. For example, the inner and outdoor panels, hoods and deck lids can be made of any combination of steel panels, aluminum panels, magnesium panels, carbon composite to satisfy structural, weight and appearance requirements of the automotive. However, the use of combination of metals presents an issue of corrosion due to galvanic action between closely spaced metal structures.

Clearly, an adhesive is a better approach than mechanical fastening. But an adhesive that comprises reservoirs encapsulated with corrosion inhibitor, as is the present invention, works even more effectively in inhibiting corrosion when two different types of metals are adhered together. Also, a curing agent encapsulated in reservoirs and added to adhesives, as provided in this invention, enables control over when the curing is desired.

D. Biocides and Antifouling Applications

Marine coatings and paint manufacturers customarily add biocides to the paint to prevent or inhibit unwanted infestation of the films by microorganisms, e.g., fungi, such as molds and yeasts, and also by bacteria, algae, and cyanobacteria (so-called "soft fouling") when these paints are applied on a vessel or underwater structure such as a pier. They have also been effective in some cases in preventing the growth of barnacles, tube worms, and the like (so-called "hard fouling"). However, the main drawback of those systems is the poor control on biocides release. Most coatings suffer from premature leakage of biocides, reducing its antifouling action before the end of coatings lifetime. Alternatively, higher biocides contents can be used to reach the required lifecycle, but the continued releasing of those toxic agents into the environment has proven to cause serious side effects on ecosystems, mainly owing to the ecotoxicity and cumulative effect of the applied bioactive agents. Therefore, rigid international regulations have been issued and more are expected to come in a near future. Therefore, ability to store biocides or antifoulants in coating for a longer time and its controlled release in coatings over time is of significant importance. Encapsulating biocides in reservoirs preserves them in the coating for a longer time, as provided in the present invention.

E. Pesticide Applications

Pesticides are undoubtedly critical elements of modern agricultural production. They can effectively increase crop yield by reducing plants pests and diseases. However, the traditional pesticide formulations have several disadvantages such as high organic solvent contents, dust drift, poor dispersibility and most importantly most of the pesticide is lost to the environment and less than 1% remains on the target. This low effectiveness contributes to serious environmental pollution associated with pesticides. Therefore, efforts should be taken to reduce waste, production cost and environmental pollution associated with pesticides while also extending the duration of pesticide activity on crops.

One of the methods to address these challenges would be by using precise controlled release of pesticides, an aspect of the present invention. This approach aims to minimize crop's demand for pesticides to gradually achieve more effective, safe pesticide usage through smart design that slows and controls pesticide release.

The present invention addresses the problems described above, and many other, in the above mentioned industries, as well as other industries further alluded to in the present disclosure. More specifically, the present invention provides a microcapsule or a micro-reservoir that is partially-open that carries an encapsulant such as a functional additive, and releases the encapsulant at a specific location, and at a specific time, immediately, or otherwise, and in many instances, as and when needed.

SUMMARY

In one aspect, this invention relates to a plurality of partially-open, hollow reservoirs:
  wherein a substantial number of said plurality of partially-open, hollow reservoirs comprises at least one encapsulant;
  wherein said plurality of partially-open, hollow reservoirs comprise a polymer comprising at least one conducting polymer;
  wherein a substantial number of said plurality of partially-open, hollow reservoirs have at least one opening on their surface, such that the average opening area, in the aggregate, of said plurality of partially-open, hollow reservoirs is from about 0.25% to about 50% of the surface area in the aggregate of said plurality of partially-open, hollow reservoirs;
  wherein the average size of said plurality of partially-open, hollow reservoirs is in the range of from about 200 nm to about 10,000 nm;
  wherein said at least one encapsulant releasably resides within said plurality of partially-open, hollow reservoirs.

In another aspect, this invention relates to the above recited plurality of partially-open, hollow reservoirs, wherein said at least one conducting polymer is selected from polyaniline-based polymer, polyaniline-based polymer derivatives, polypyrrole, polypyrrole based polymer, polypyrrole based polymer's derivatives, blends thereof, and mixtures thereof.

In yet another aspect, this invention relates to the above recited plurality of partially-open, hollow reservoirs, wherein said conducting polymer is the polyaniline-based polymer, comprising at least one of polyaniline, poly-o-toluidine, poly-o-methoxyaniline, poly-o-ethylaniline, and poly-2-ethoxyaniline In a further aspect, this invention relates to the above recited plurality of partially-open, hollow reservoirs, wherein the plurality of partially-open, hollow reservoirs comprises the at least one polyaniline-based polymer in its base form, in its salt form, or in a blend of its base form and its salt form.

In one aspect, this invention relates to the above recited plurality of partially-open, hollow reservoirs, wherein the at least one polyaniline-based polymer is in its emeraldine form, in its leucoemeraldine form, or in its pernigraniline form, or a combination thereof.

In another aspect, this invention relates to the above recited plurality of partially-open, hollow reservoirs, wherein said encapsulant is selected from the group consisting of a corrosion inhibiting additive, a lubricant additive, an adhesive additive, a biocide additive, an antifouling additive, a pesticide additive, a drug delivery additive, a corrosion sensor additive, a fragrance releasing additive, a catalyst additive, an ink additive, a dye additive, an enzyme additive, a reactant additive, and combinations thereof.

In yet another aspect, this invention relates to the above recited plurality of partially-open, hollow reservoirs, wherein said corrosion inhibiting additive is selected from (a) an organic compound containing an amino group or carboxy group or salts of carboxylic acids, organic sulfides, heterocyclic rings, substituted aromatic rings, organic phosphates and phosphonic acids, quaternary ammonium compounds, imidazolines, aldehydes, sulfoxides, carboxylic acids, mercaptocarboxylic acids, imidazoles, oximes, azoles, tannins, substituted phenols, quinoline and quinolone compounds, substituted quinolines and quinalizarin, pyridinium group, pyrazine group, an azole derivative, and, one or more schiffs bases; (b) an organic compound containing one or more anions selected from the group comprising polyphosphate and its derivatives, nitrite, silicate, molybdate, and polymolybdate and its derivatives, vanadate and polyvanadate and its derivatives; and (c) an organic or inorganic compound comprising one or more cations selected from the group comprising lanthanides, magnesium, calcium, titanium, zirconium, yttrium, chromium and silver; combinations of components within each corrosion inhibiting additive group (a), (b), and (c); and combinations between one or more components of each additive group (a), (b), and (c).

In a further aspect, this invention relates to the above recited plurality of partially-open, hollow reservoirs, wherein said encapsulant is a lubricant additive selected from: (i) antioxidant additives selected from phenols and its derivatives, aromatic and aryl amines; (ii) anti-wear additives selected from metal alkyltiophosphate; (iii) dispersants selected from of phenates, sulfurized phenates, salicylates, naphthenates, stearates, carbamates, thiocarbamates, phosphorous derivatives; combinations of components within each lubricant additive group (i), (ii), and (iii); and combinations between one or more components of each lubricant additive group (i), (ii), and (iii).

In one aspect, this invention relates to the above recited plurality of partially-open, hollow reservoirs, wherein said encapsulant is an adhesive additive selected from the following corrosion inhibitor encapsulants: chromate compositions, phosphates, silicates, nitrates, benzoates, mercaptobenzothiazoles, sodium molybdate formulations, phosphonic acids combined with amines, and combinations thereof.

In another aspect, this invention relates to a matrix comprising the plurality of partially-open, hollow reservoir as recited above.

In yet another aspect, this invention relates to the above recited plurality of partially-open, hollow reservoirs, wherein said partially-open, hollow reservoirs are nominally spherical-shaped hollow reservoirs, nominally rod-shaped hollow reservoirs, irregular-shaped hollow reservoirs, or a hollow micro-particles with more than one opening.

In a further aspect, this invention relates to a process for preparing the plurality of the partially-open, hollow reservoirs as recited above, but devoid of any encapsulant, wherein said conducting polymer is the polyaniline-based polymer, comprising the step of polymerizing a monomer of the polyaniline-based polymer by aqueous oxidative polymerization.

In another aspect, this invention relates to a process for preparing the plurality of the partially-open, hollow reservoirs as recited above;
comprising the steps of:
(A1) preparing a plurality of partially-open, hollow reservoirs devoid of any encapsulant; and
(A2) encapsulating the at least one encapsulant by (a) solvent evaporation; or (b) precipitation method; OR
comprising the step of:
(B1) in-situ encapsulation of encapsulant during the polymerization process of partially-open, hollow reservoirs.

In yet another aspect, this invention relates to the process as recited above, wherein said conducting polymer is at least one polyaniline-based polymer.

In a further aspect, this invention relates to the process as recited above, wherein said at least one polyaniline-based polymer is in its base form, or in its salt form, or in a blend of its base form and its salt form.

In one aspect, this invention relates to the process as recited above, wherein said at least one polyaniline-based polymer is in its emeraldine form or its leucoemeraldine form or pernigraniline form.

In another aspect, this invention relates to the process as recited above, wherein said encapsulant is selected from the group consisting of a corrosion inhibiting additive, a lubricant additive, an adhesive additive, a biocide additive, an antifouling additive, a pesticide additive, a drug delivery additive, a corrosion sensor additive, a fragrance releasing additive, a catalyst additive, an ink additive, a dye additive, an enzyme additive, a reactant additive, and combinations thereof.

In yet another aspect, this invention relates to a process for preparing a matrix comprising the plurality of partially-open, hollow reservoir as recited above, comprising the steps of:
(1) contacting said POHR with said matrix, and optionally
(2) mixing said POHR in said matrix.

In a further aspect, this invention relates to the process described above, wherein said matrix is a paint or a coating, and said encapsulant is a corrosion inhibitor.

In one aspect, this invention relates to a process for preparing the plurality of partially-open, hollow reservoirs as recited above, comprising the step of in-situ encapsulation of the at least one encapsulant inside the plurality of the partially-open, hollow reservoirs during synthesis of said plurality of the partially-open hollow reservoirs.

In another aspect, this invention relates to a process for releasing the at least one encapsulant from the plurality of the partially-open, hollow reservoirs as recited previously, comprising the step of providing external stimuli to the plurality of the partially-open, hollow reservoirs; wherein the external stimuli is at least one of the following:
(1) changing the pH of the environment of the plurality of the partially-open, hollow reservoirs;
(2) changing the redox potential of the plurality of the partially-open, hollow reservoirs;
(3) changing the oxidation state of the plurality of the partially-open, hollow reservoirs;
(4) mechanically damaging the plurality of the partially-open, hollow reservoirs;
(5) changing the voltage applied to the plurality of the partially-open, hollow reservoirs; and
(6) changing the electrochemical potential of the plurality of the partially-open, hollow reservoirs.

In yet another aspect, this invention relates to a process for inhibiting corrosion in metal, comprising the step of coating said metal with a coating matrix comprising the partially-open, hollow reservoirs as recited above, wherein said at least one encapsulant comprises at least one corrosion inhibitor.

In a further aspect, this invention relates to the process as recited above, wherein said at least one corrosion inhibitor is selected from (a) an organic compound containing an amino group or carboxy group or salts of carboxylic acids, organic sulfides, heterocyclic rings, substituted aromatic rings, organic phosphates and phosphonic acids, quaternary ammonium compounds, imidazolines, aldehydes, sulfoxides, carboxylic acids, mercaptocarboxylic acids, imidazoles, oximes, azoles, tannins, substituted phenols, quinoline and quinolone compounds, substituted quinolines and quinalizarin, pyridinium group, pyrazine group, an azole derivative, and, one or more schiffs bases; (b) an organic compound containing one or more anions selected from the group comprising polyphosphate and its derivatives, nitrite, silicate, molybdate, and polymolybdate and its derivatives, vanadate and polyvanadate and its derivatives; and (c) an organic or inorganic compound comprising one or more cations selected from the group comprising lanthanides, magnesium, calcium, titanium, zirconium, yttrium, chromium and silver; combinations of components within each corrosion inhibiting additive group (a), (b), and (c); and combinations between one or more components of each additive group (a), (b), and (c).

In one aspect, this invention relates to the process as recited above, wherein the matrix coating is latexes, amino resins, polyurethanes, epoxies, phenolic resins, acrylic resins, polyester resins, alkyd resins, polysulfide resins, polyaspartic, polyurea, polylactones, adducts of amines, polyimide, polycarbonate and halogenated polymer resins.

In another aspect, this invention relates to the process as recited above, wherein said metal is part of an automotive, an automotive part, part of a marine vehicle, a refinish part, a marine vehicle part, part of an equipment, an equipment part, part of a metal cladding, a metal cladding part, part of any other vehicle, a part for any other vehicle, a part of a flying object, a part for a flying object, a part of a decorative piece, and a part for a decorative purpose, industrial machinery, industrial machinery parts, pipes, pipe parts, tanks, tank parts, bridges, and bridge parts, coils, architecture and architecture parts, metal equipment and structures used in power sector, metal equipment and structures used in energy sector, and metal equipment and structures used in transportation sectors.

In yet another aspect, this invention relates to the process recited above, wherein said matrix is a lubricant and said encapsulant is a lubricant additive selected from: (i) anti-oxidant additives selected from phenols and its derivatives, aromatic and aryl amines; (ii) anti-wear additives selected from metal alkyltiophosphate; (iii) dispersants selected from of phenates, sulfurized phenates, salicylates, naphthenates, stearates, carbamates, thiocarbamates, phosphorous derivatives; combinations of components within each lubricant additive group (i), (ii), and (iii); and combinations between one or more components of each lubricant additive group (i), (ii), and (iii).

In a further aspect, this invention relates to the process recited previously, wherein said matrix is an adhesive, wherein said encapsulant is an adhesive additive selected from the following corrosion inhibitor encapsulants: chromate compositions, phosphates, silicates, nitrates, benzoates, mercaptobenzothiazoles, sodium molybdate formulations, phosphonic acids combined with amines, and combinations thereof.

BRIEF DESCRIPTION OF THE DRAWINGS

FIG. 1.1: A scanning electron micrograph (SEM) of micro-reservoirs of a variety of shapes and surface openings;

FIG. 1.2: A scanning electron micrograph (SEM) of micro-reservoirs of a variety of shapes and surface openings;

FIG. 9.1: Digital images of steel panels coated with coatings after ASTM B117 Salt-Fog Test; Primer: (a) Acrylic coating, no micro-reservoirs, control sample, after 360 hours; (b) Acrylic coating containing 3 wt. % Halox 570, after 264 hours; (c) Acrylic coating containing 3 wt. % POT micro-reservoirs encapsulated with Halox 570, after 2040 hours;

DETAILED DESCRIPTION OF ILLUSTRATIVE EMBODIMENTS

Figure 2:
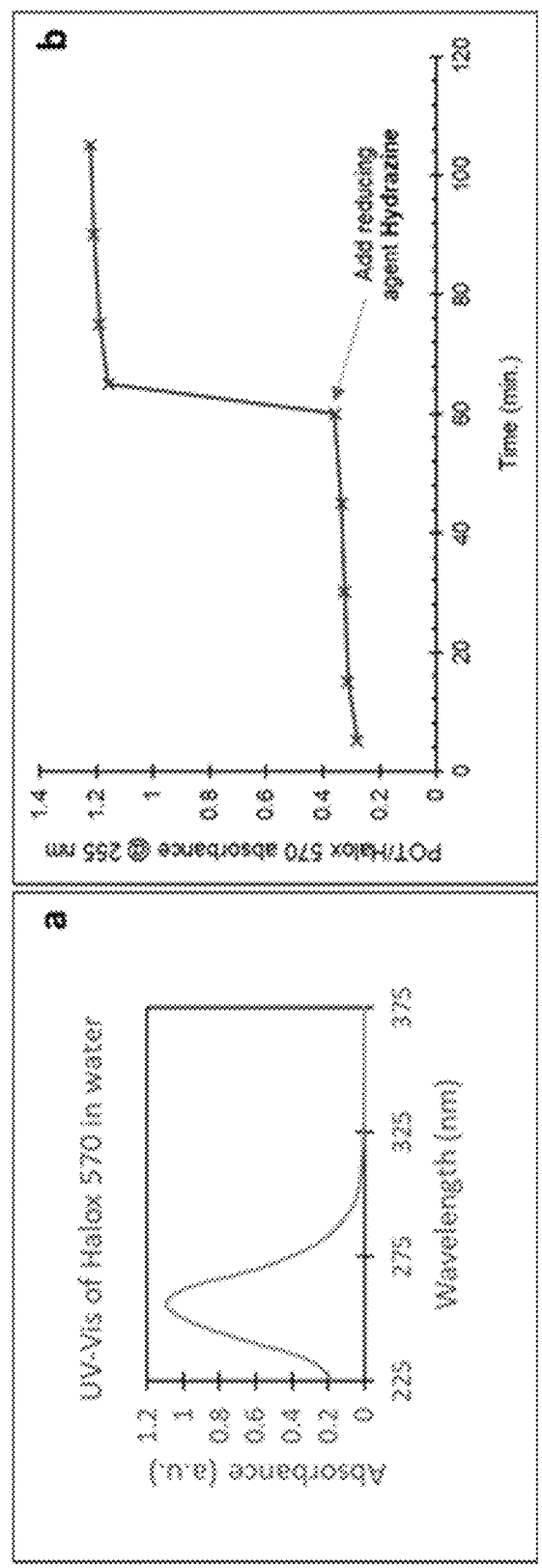
FIG. 2: UV-Vis Absorbance as function of time to determine the release of corrosion inhibitor from micro-reservoirs upon reduction; (a) UV-Vis Absorbance spectra of Halox 570; (b) Absorbance of Halox 570 released from micro-reservoirs as a function of time before and after reduction of the micro-reservoirs.

The present invention pertains to polymer-based, partially-open, hollow reservoirs that can release an encapsulant immediately in-response to external stimuli. External stimuli include reduction/oxidation, pH change, voltage change, and change in electrochemical potential. In another embodiment the encapsulant can also be released by mechanical damage or shearing of the walls of the partially-open, hollow reservoirs. Alternatively, the partially-open, hollow reservoirs can also release the encapsulant gradually, as opposed to immediately, over time, as a result of the partially-open configuration of the partially-open, hollow reservoirs.

(A) Partially-Open, Hollow Reservoirs

By partially-open, hollow reservoirs (POHR) is meant structures that have at least one opening on its surface, and a hollow interior that can optionally be a repository or storage of one or more encapsulants. Preferably, the POHR of the present invention are polymer-based. By "partially-open" in the present disclosure is meant that in a plurality of the POHR, a substantial number have at least one opening on its surface. It can also have two, or three, or four, or multiple openings on its surface. FIG. 1 shows a schematic of various partially-open POHR of the present invention. In this disclosure, POHR, reservoirs, micro-reservoirs, and nano-reservoirs, and microcapsules are used interchangeably. They mean the one and the same structure. In a plurality of micro-reservoirs, it is possible that a nominal amount of the micro-reservoirs are closed structures.

In one embodiment, the POHR are polymer-based structures. In one embodiment, the polymer comprises a conducting polymer. In one embodiment, the polymer is a blend or a mixture of two or more polymers, with at least one of the polymers comprising a conducting polymer.

In one embodiment, the polymer comprises polyaniline-based polymer, and/or its derivatives, and/or its oligomers. In one embodiment, the polymer comprises polyaniline, or poly-o-methoxyaniline, or poly-o-toluidine. In one embodiment, the conducting polymer is polypyrrole and/or its derivatives, and/or its oligomers. This invention also envisions a polymer comprising copolymers of the polyaniline-based polymer, and a polymer comprising copolymers of polypyrrole-based polymer.

The POHR of the present invention have an average size ranging from 200 nm to 10,000 nm (10 μm) in effective diameter. In other words, the average size of a plurality of the POHR is any one of the following numbers, in nm: 200, . . . , 250, . . . , 300, . . . , 350, . . . , 400, . . . , 450, . . . , 500, . . . , 550, . . . , 600, . . . , 650, . . . , 700, . . . , 750, . . . , 800, 850, . . . , 900, . . . , 950, . . . , 1000, . . . , 2000, . . . , 3000, . . . , 4000, . . . , 5000, . . . , 6000 7000, . . . , 8000, . . . , 9000, . . . , 9500, . . . , 9550, . . . , 9600, . . . , 9650, . . . , 9700, . . . , 9750, . . . , 9800, . . . , 9850, . . . , 9900, . . . , 9950, . . . , and 10000.

In one embodiment, the average size of the POHR is in the range defined by any two numbers above, including the endpoints. By the spacing in between two numbers above is meant that the intermediate numbers are also disclosed herein. The spacing is provided simply for brevity.

In one embodiment, a combination of POHR with one or more and a variety of openings allows for a desired release profile of the encapsulant. For example, in one embodiment, the present invention provides for microreservoirs that have an opening in the range of 0.25% to about 50% of the surface area of an effective sphere having equivalent surface area as a POHR microreservoir. In other words, the average size of the opening in percentage terms can be any number from the list below: 0.25, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

In one embodiment, the average size of the openings is within a range defined by any two numbers given above, including the endpoints. A desired distribution of microreservoir opening sizes can be prepared, for example, by blending two or more batches of such microreservoirs. For example, in one distribution, the 25% of the microreservoirs have 20% average opening size, 25% microreservoirs have 30% average opening size, 25% microreservoirs have 35% average opening size, and 25% microreservoirs have 40% average opening size. FIG. 1 shows an SEM image of micro-reservoirs of the present invention with various opening sizes.

The reservoirs can be of variety of shapes such as capsular, spherical, tubular, and porous hollow particulates (See FIG. 1.1, 1.2). In one embodiment, generally the POHR are irregular spheres with one or more openings or pores or holes on their surface. In many embodiments, the spheres are not fully formed, which contributes to providing the partial openness of the POHR. In one embodiment, the POHR have multiple openings on the surface, wherein the openings have a mesh-like structure, at least partially, on the surface of the micro-reservoirs. See for example, FIG. 1.

(B) Encapsulants

By encapsulant is meant an additive, generally soluble in a solvent—for example, an organic solvent—that is incorporated or encapsulated in the partially-open, hollow reservoirs (POHR), and which is generally available for release at a later point in time, as a result of external stimuli, or as a result of mechanical damage to the POHR, or a gradual release over time. The encapsulant can be a functional additive, or a non-functional additive. The encapsulant is soluble or can be dispersed in organic, inorganic, or aqueous media. Dispersion includes colloidal suspensions, emulsions, and the like. Generally, the encapsulant resides in, or is encapsulated in, the hollow interior of the POHR. Because the POHR "gates open" upon a chemical signal or a stimuli as explained supra, one can view the encapsulant as being "chemically entrapped" inside the POHR.

Separately, however, this invention also envisions the encapsulant being adsorbed on the external surface of the POHR. The process of encapsulation in the partially-open, hollow reservoirs is described infra.

In one embodiment of the invention, the POHR comprise at least one type of encapsulant. For example, the POHR may comprise an encapsulant E1. In another example, the POHR may comprise two encapsulants, E1 and E2, and so on and so forth. To be clear, what is meant for this embodiment is that, generally, each microreservoir comprises both encapsulants, for example, E1 and E2.

In another embodiment, a substantial percent of POHR comprises at least one type of encapsulant, while some of the POHR may not have any encapsulant. For example, substantial percent of the POHR comprises the encapsulant E1, and some POHR may not have any encapsulant. In another example, a substantial percent of the POHR comprise both encapsulants E1 and E2, and some POHR may not have any encapsulant.

In yet another embodiment, some of the partially-open, hollow reservoirs (POHR) have one type of encapsulant, some POHR have another type of encapsulant, some other POHR have yet another type of encapsulant, and so on, and so forth. For example, some POHR comprise encapsulant E1, some POHR comprise encapsulant E2, and some other POHR comprise encapsulant E3.

In one embodiment, in a given plurality of POHR, a first set of the POHR may have one or more type of encapsulants, a second set of the POHR may have one or more type of encapsulants, but at least one encapsulant is a different type of encapsulant between the two sets. For example, the first set may have encapsulant E1, and the second set may have encapsulant E2; or the first set may have encapsulants E1 and E2, and the second set may have the encapsulant E2; or the first set may have encapsulants E1, E2, and E3, and the second set may have encapsulants E2 and E3. Similarly, this embodiments envisions a plurality of POHR comprising multiple sets of POHR, wherein each set of POHR has one or more encapsulants, such that at least one encapsulant is different between any two sets of POHR comprising such encapsulants.

Stated another way, if Pi represent various sets of POHR, and Ej represent various types of encapsulants, this invention envisions various one or more sets of POHR, comprising one or more encapsulants:

$$\Sigma P_i(\Sigma E_j)$$

wherein the parenthesis signifies encapsulation;
Pi is a set of POHR, wherein i varies from 1-10;
Ej is an encapsulant, wherein j varies from 1-10; and
Σ denotes addition.

Encapsulants with many functionalities, vel non, can be added to a POHR. Such functional additives include: corrosion inhibiting additives; lubricant additives; adhesive additives; biocidal additives; anti-fouling additives; pesticide additive; drug delivery additive; vapor sensor additive; chemical sensor additive; bio-sensor additive; food-packaging sensor; corrosion sensor; fragrance release additive; catalyst additive; enzyme additive; pH balancing additive; color additive; tint additive, charge dissipation additive; ink refreshing additive, and static removing additive.

Non-exhaustive list of useful solvents useful for solubilizing or dispersing the encapsulants are provided in Table 1.

TABLE 1

Solvents for Encapsulation
Common solvents used for the encapsulants of the present invention include the ones in the following table:

| Solvent | Formula | MW | boiling point (° C.) | melting point (° C.) | density (g/mL) | solubility in water (g/100 g) | Dielectric Constant[3,4] | flash point (° C.) |
|---|---|---|---|---|---|---|---|---|
| acetic acid | $C_2H_4O_2$ | 60.052 | 118 | 16.6 | 1.0446 | Miscible | 6.20 | 39 |
| benzene | $C_6H_6$ | 78.11 | 80.1 | 5.5 | 0.8765 | 0.18 | 2.28 | −11 |
| 1-butanol | $C_4H_{10}O$ | 74.12 | 117.7 | −88.6 | 0.8095 | 6.3 | 17.8 | 37 |
| 2-butanol | $C_4H_{10}O$ | 74.12 | 99.5 | −88.5 | 0.8063 | 15 | 17.26 | 24 |
| 2-butanone | $C_4H_8O$ | 72.11 | 79.6 | −86.6 | 0.7999 | 25.6 | 18.6 | −9 |
| t-butyl alcohol | $C_4H_{10}O$ | 74.12 | 82.4 | 25.7 | 0.7887 | Miscible | 12.5 | 11 |
| chlorobenzene | $C_6H_5Cl$ | 112.56 | 131.7 | −45.3 | 1.1058 | 0.05 | 5.69 | 28 |
| cyclohexane | $C_6H_{12}$ | 84.16 | 80.7 | 6.6 | 0.7739 | 0.0055 | 2.02 | −20 |
| diethylene glycol | $C_4H_{10}O_3$ | 106.12 | 246 | −10 | 1.1197 | 10 | 31.8 | 124 |
| diethyl ether | $C_4H_{10}O$ | 74.12 | 34.5 | −116.2 | 0.713 | 7.5 | 4.267 | −45 |
| diglyme (diethylene glycol dimethyl ether) | $C_6H_{14}O_3$ | 134.17 | 162 | −68 | 0.943 | Miscible | 7.23 | 67 |
| 1,2-dimethoxy-ethane (glyme, DME) | $C_4H_{10}O_2$ | 90.12 | 84.5 | −69.2 | 0.8637 | Miscible | 7.3 | −2 |
| 1,4-dioxane | $C_4H_8O_2$ | 88.11 | 101.1 | 11.8 | 1.033 | Miscible | 2.21 (25) | 12 |
| ethanol | $C_2H_6O$ | 46.07 | 78.5 | −114.1 | 0.789 | Miscible | 24.6 | 13 |
| ethyl acetate | $C_4H_8O_2$ | 88.11 | 77 | −83.6 | 0.895 | 8.7 | 6 (25) | −4 |
| ethylene glycol | $C_2H_6O_2$ | 62.07 | 195 | −13 | 1.115 | Miscible | 37.7 | 111 |
| glycerin | $C_3H_8O_3$ | 92.09 | 290 | 17.8 | 1.261 | Miscible | 42.5 | 160 |
| heptane | $C_7H_{16}$ | 100.20 | 98 | −90.6 | 0.684 | 0.01 | 1.92 | −4 |
| Hexamethylphosphoramide (HMPA) | $C_6H_{18}N_3OP$ | 179.20 | 232.5 | 7.2 | 1.03 | Miscible | 31.3 | 105 |
| Hexamethylphosphorous triamide (HMPT) | $C_6H_{18}N_3P$ | 163.20 | 150 | −44 | 0.898 | Miscible | ?? | 26 |
| hexane | $C_6H_{14}$ | 86.18 | 69 | −95 | 0.659 | 0.0014 | 1.89 | −22 |
| methanol | $CH_4O$ | 32.04 | 64.6 | −98 | 0.791 | Miscible | 32.6 (25) | 12 |
| methyl t-butyl ether (MTBE) | $C_5H_{12}O$ | 88.15 | 55.2 | −109 | 0.741 | 5.1 | ?? | −28 |
| nitromethane | $CH_3NO_2$ | 61.04 | 101.2 | −29 | 1.382 | 9.50 | 35.9 | 35 |
| pentane | $C_5H_{12}$ | 72.15 | 36.1 | −129.7 | 0.626 | 0.04 | 1.84 | −49 |
| Petroleum ether (ligroine) | — | — | 30-60 | −40 | 0.656 | — | — | −30 |
| 1-propanol | $C_3H_8O$ | 60.10 | 97 | −126 | 0.803 | Miscible | 20.1 (25) | 22 |
| 2-propanol | $C_3H_8O$ | 60.10 | 82.4 | −88.5 | 0.785 | Miscible | 18.3 (25) | 12 |
| pyridine | $C_5H_5N$ | 79.10 | 115.2 | −41.6 | 0.982 | Miscible | 12.3 (25) | 17 |
| toluene | $C_7H_8$ | 92.14 | 110.6 | −93 | 0.867 | 0.05 | 2.38 (25) | 4 |
| triethyl amine | $C_6H_{15}N$ | 101.19 | 88.9 | −114.7 | 0.728 | 0.02 | 2.4 | −11 |
| water | $H_2O$ | 18.02 | 100.00 | 0.00 | 0.998 | — | 78.54 | — |
| water, heavy | $D_2O$ | 20.03 | 101.3 | 4 | 1.107 | Miscible | ?? | — |
| o-xylene | $C_8H_{10}$ | 106.17 | 144 | −25.2 | 0.897 | Insoluble | 2.57 | 32 |
| m-xylene | $C_8H_{10}$ | 106.17 | 139.1 | −47.8 | 0.868 | Insoluble | 2.37 | 27 |
| p-xylene | $C_8H_{10}$ | 106.17 | 138.4 | 13.3 | 0.861 | Insoluble | 2.27 | 27 |

(C) Method of Preparing Partially-Open, Hollow Reservoirs

In one embodiment, the conducting polymer-based micro-reservoirs, for example, of polyaniline, poly-o-toluidine and poly-o-methoxyaniline are synthesized by chemical oxidative polymerization of their respective monomer in aqueous media using ammonium peroxydisulfate as oxidant.

The micro-reservoirs have at least one hole or an opening on the surface that enables encapsulation of encapsulant after the polymeric micro-reservoirs are synthesized. Once the encapsulant is encapsulated or incorporated in the partially-open, hollow reservoirs (POHR), the openings, also known as holes or orifices, enable the release of the encapsulant, either by external stimuli, mechanical shear or abrasion, or a sustained or a gradual release of encapsulant over time.

Polyaniline

In one embodiment, the polymer used for preparing the POHR comprises polyaniline-based polymer prepared from the polymerization of substituted or unsubstituted aniline. When the term "aniline" is used herein, it is used generically to include substituted and unsubstituted anilines, unless the context is clear that only the specific non-substituted form is intended. In general, anilines for use in the invention are monomers of the Formula I below, wherein:

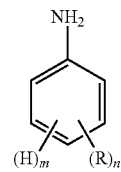

Formula I m is an integer from 1 to 5;
n is an integer from 0 to 4, with the proviso that the sum of m and n is equal to 5; and
R is independently selected so as to be the same or different at each occurrence and is selected from the group consisting of alkyl, alkenyl, alkoxy, cycloalkyl, cycloalkenyl, alkanoyl, alkythio, aryloxy, alkylthioalkyl, alkylaryl, arylalkyl, amino, alkylamino, dialkylamino, aryl, alkylsulfinyl, alkoxyalkyl, alkylsulfonyl, arylthio, arylsulfinyl, alkoxycarbonyl, arylsulfonyl, carboxylic acid, halogen, cyano, or alkyl substituted with one or more sulfonic aid, carboxylic acid, halo, nitro, cyano or expoly moieties; or carboxylic acid, halogen, nitro, cyano, or sulfonic acid moieties; or any two R groups together may form an alkylene or alkenylene chain completing a 3, 4, 5, 6 or 7-membered aromatic or alicyclic ring, which ring may optionally include one or more divalent nitrogen, sulfur or oxygen atoms. Without intending to limit the scope of this invention, the size of the various R groups ranges from about 1 carbon (in the case of alkyl) through 2 or more carbons up through about 20 carbons with the total of n Rs being from about 1 to about 40 carbons.

The following listing of substituted and unsubstituted anilines are illustrative of those which can be used to prepare polymers and copolymers useful in the practice of this invention: Aniline; 2,5-Dimethylaniline; o-Toluidine; 2,3-Dimethylaniline; m-Toluidine; 2,5-Dibutylaniline; o-Ethylaniline; 2,5-Dimethoxyaniline; m-Ethylaniline; Tetrahydronaphthylamine; o-Ethoxyaniline; o-Cyanoaniline; m-Butylaniline; 2-Thiomethylanilinem-Hexylaniline; 2,5-Dichloroaniline; m-Octylaniline; 3-(n-Butanesulfonic acid) aniline; 2-Bromoaniline; 3-Bromoaniline; 2,4-Dimethoxyaniline; 3-Acetamidoaniline; 4-Bromoaniline; 4-Mercaptoaniline; 4-Acetamidoaniline; 4-Methylthioaniline; 5-Chloro-2-methoxyaniline; 3-Phenoxyaniline; 5-Chloro-2-ethoxyaniline; 4-Phenoxyaniline.

In one embodiment of the invention the structure of polyaniline and its derivatives is shown below. In the present invention, the polyaniline and its derivatives are used as microreservoirs in both conducting configuration, also known as the doped configuration, and insulating configuration, also known as undoped configuration:

Formula II

The above formula depicts the structure of the polymer backbone that is used to prepare one embodiment of the partially-open, hollow microreservoir or capsule of the present invention. For example, when R=H, the structure is of polyaniline. For $R_1=CH_3$, $R_2=H$, it is poly-o-toluidine, and for $R=C_2H_2$, $R_2=H$, it is poly-2-ethylaniline. For $R=OCH_3$, $R_2=H$, it is poly-o-methoxyaniline and for $R=OC_2H_5$, $R_2=H$, it is poly-ethoxyaniline. For $R_1=CH_3$, $R_2=CH_3$, it is poly-2,5-dimethylaniline and for $R_1=C_3H_5$, $R_2=C_2H_5$, it is poly-2,5-diethylaniline. For $R_1=OCH_3$, $R_2=OCH_3$, it is poly-2,5-dimethoxyylaniline and for $R_1=OC_2H_5$, $R_2=OC_2H_5$, it is poly-2,5-diethoxylaniline. The structure designated as (a) corresponds to the conducting or the doped configuration of the polyaniline-based polymer, wherein D is the dopant counterion. The structure designated as (b) corresponds to the insulating or undoped configuration of the backbone molecule, without the dopant counterion.

In one embodiment of the present invention, the POHR are based on polyaniline and its derivatives, and can be used in their both conducting and insulating form. Depending on the concentration of monomer and oxidant, reservoirs are obtained with size ranging from 200 nm to 10,000 nm (10 μm) in diameter.

In one embodiment, an aniline-based monomer for example, o-toluidine monomer is oxidatively polymerized in aqueous medium using ammonium peroxydisulfate oxidant under controlled temperature conditions in the below-room-temperature range The reaction is generally left undisturbed, in icy conditions for a few hours. Reservoirs of different size and shapes are synthesized by changing the concentration of the monomer and the oxidant, and the temperature of the reaction mixture. As the monomers are dispersed in the aqueous medium, they form micro-emulsions in the aqueous medium. When the oxidant is added, the monomer polymerizes such that it forms the partially-open hollow reservoir of the invention.

Reservoirs of different size and shapes are synthesized by changing the concentration of the monomer and oxidant. Reaction conditions of temperature, and concentration of the reactants can be tailored to engender a particular shape of the reservoirs of the present invention (self-assembly of polymerizing chains), such as partially-open hollow reservoirs, tubes, nanofibrous structures, and porous and hollow structures.

(D) Method of Encapsulating the Encapsulant in the POHR

In one embodiment of the present invention, the additives or encapsulants are encapsulated in the partially-open, hollow reservoirs, by three methods namely: (a) solvent evaporation; (b) in-situ deposition; and (c) precipitation.

(a) Solvent Evaporation Method

In this method, a saturated encapsulant solution is prepared in its volatile solvent. Partially-open, hollow reservoirs (POHR) are added to the encapsulant solution and stirred for few hours to ensure that the encapsulant solution seeps inside the POHR, or is sufficiently adsorbed. The solution is then heated to remove the solvent resulting in reservoirs encapsulated with the encapsulant. Clearly, one or more types of encapsulants can be used as long as the solvent is amenable to preparing a solution of the one or more types of encapsulants.

(b) In-Situ Deposition Method

In this method, the encapsulant is added during the synthesis of the partially-open, hollow microreservoirs (POHR). Due to interaction of encapsulant moieties and monomer, the encapsulant moiety enters the monomer micelles formed during polymerization, resulting in formation of POHR encapsulated with the encapsulant. Clearly, one or more types of encapsulants can be used for the in situ deposition of the encapsulant. This technique does not necessarily require that the encapsulant be dissolved in a solvent to form a solution.

(c) Precipitation Method

In this method, a saturated encapsulant solution is prepared in a water miscible solvent. POHR are added to the encapsulant solution and stirred for few hours to make sure that the encapsulant solution seeps inside the POHR, or is sufficiently adsorbed. The solution is then added to ice-cold water such that the encapsulant precipitates out of the solution resulting in encapsulant encapsulated within the micro-reservoirs. The solvent and water are removed by standard methods.

(E) Method of Releasing the Encapsulant from the POHR

The encapsulant release from the partially-open, hollow reservoirs (POHR) can be triggered by oxidation, reduction, pH change, voltage change, and/or electrochemical potential, and/or mechanical damage, v. Mechanical damage, for example, by shear or force can also release the encapsulant. The encapsulant can also be released, over time, from the one or more openings in the POHR.

In one embodiment, the POHR in combination with the above mentioned release stimuli or triggers determine the rate and the release of the encapsulant at a given time. Stated another way, the present invention provides a mechanism for time release of encapsulants with the partial opening in the POHR assisting in the time-dependent release of the encapsulants. In one embodiment, a combination of POHR with a variety of openings allows for a desired release profile. For example, one embodiment provides for POHR that have an opening in the range of 0.25% to about 50% of the surface area of an effective sphere having equivalent surface area as a POHR microreservoir. In other words, the average size of the opening in percentage terms can be any number from the list below: 0.25, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50.

In one embodiment, the average size of the openings is within a range defined by any two numbers given above, including the endpoints.

In one embodiment, a desired distribution of microreservoir opening sizes can be prepared. For example, in one distribution, the 25% of the POHR have 20% average opening size, 25% POHR have 30% average opening size, 25% POHR have 35% average opening size, and 25% POHR have 40% average opening size. FIG. 1 shows an SEM image of POHR of the present invention with various opening sizes.

The encapsulant are released instantaneously, from the POHR, at-will, based on external stimuli; or over a period of time, due to the one or more openings on the POHR surface.

In the present invention, the release of an encapsulant, such as a functional additive, does not depend simply on the one or more openings of the POHR. In other words, the partial openness signified by the one or more openings on the POHR is not the only, or the substantial, consideration for releasing the encapsulant into the medium or the matrix embodying the POHR comprising the encapsulant. In fact, the plausible mechanism that the present invention uses is a 'chemical shear" that engenders the release of the encapsulant, in conjunction with the partial openness of the POHR. Substantially, it is the externally induced change in the reduction-oxidation state of the base polymer, or the change in electrochemical potential, or a change in the pH, or a change in voltage that acts as external stimuli that releases the encapsulant. This is shown in FIG. 2b. A step-change in release occurs as a result of the change in oxidation state (reduction of the moieties occurs). In one embodiment, this invention provides substantially a chemical impact in minor conjunction with a mechanical shear and/or the partial openness of the POHR (as opposed to substantially, or only, a mechanical impact, for example a mechanical shear), which aids in releasing the functional additive inside the polymeric micro-reservoir. Alternatively, this phenomenon of a "chemical" stimuli that releases the encapsulant such as a functional additive is called "chemical shear" for the purposes of the present invention.

The ability to release contents from reservoirs in a controlled manner is of significant interest in a variety of applications such as self-healing coatings, lubricants, corrosion inhibition, antimicrobial protection, drug delivery, sensors, fragrance release, fertilizer release, pesticide release, inks, dyes for billboards and signs, catalysis, and battery repair.

Reservoirs can either act as carriers or delivery vehicles to deliver its encapsulants at a specific site and/or time, or be used to store specialty chemicals that will be released as and when required. Adding the functional additives to a medium, as encapsulated within the POHR, increases the functional life of such additives in the medium when compared to the life of the same additive that is added directly—that is, without encapsulation in a POHR, —because the encapsulated configuration protects the additives from leaching out or from being consumed up too rapidly.

Depending on the POHR polymer backbone structure, various mechanisms can initiate changes in reservoir shell wall that can provide a trigger to release the POHR contents. Changes in pH or presence of certain chemicals can also trigger release of encapsulant that can be useful in drug or drug precursor delivery to specific locations in a subject such as a human or an animal or other species requiring such administration. Electrically or electrochemically-induced release of encapsulants are useful in anticorrosive coating or battery repair.

Polymer-based reservoirs of the core-shell type release their encapsulant upon mechanical damage. The polymer reservoirs that are sensitive to external triggers and release encapsulant on external stimulus need modification of polymer backbone with some chemical or physical functionalities to make it sensitive to external trigger. However, the POHR of the present invention, comprising polyaniline and its derivatives are intrinsically conductive polymers that are electroactive and can convert from conducting to insulating from by acid base redox chemistry. Therefore, conducting polymer reservoirs do not require polymer backbone modification to incorporate sensitivity to external triggers for encapsulant release.

(F) Polyaniline Encapsulant Release Mechanism

The above formula depicts the chemical structure of polyaniline emeraldine salt (conducting) and emeraldine base (insulating) form and its different oxidation states—pernigraniline and leucoemeraldine.

The inventors propose the following theory, without wishing to be bound by it, as it relates to the present invention. Polyaniline is an intrinsically conducting polymer that can be converted from conducting to insulating form by simple acid base redox chemistry. Also, similar to metals, polyaniline can be converted from one oxidation state to another, i.e., polyaniline can exist in three oxidation states—leucoemeraldine, emeraldine and pernigraniline of which emeraldine oxidation state is the stable form. The release of encapsulant from polyaniline can be attributed to its redox property to convert from conducting to insulating form or the ability to go from one oxidation state to another.

Polyaniline reservoirs in the emeraldine oxidation state stores the organic moieties inside it, while in the reduced oxidation state releases the organic moieties. In the emeraldine oxidation state, polyaniline contains benzenoid rings and quinonoid rings. This makes the polymer chains more compact due to amine-imine intermolecular hydrogen bonding thereby hindering the release of organic moieties stored inside it. When polyaniline is reduced to leucoemeraldine oxidation state, the hydrogen bonding becomes weaker and the absence of double bonds of the quinonoid rings decreases the rigidity of polyaniline chain. Therefore, due to weak hydrogen bonding (less compact structure) and flexibility of polymer chains, polyaniline in the leucoemeraldine oxidation state is more permeable and porous that can release organic moieties stored inside the reservoirs.

Polyaniline chain in the leucoemeraldine oxidation is more flexible is also evident by the light scattering and gel permeation chromatography studies. It is observed that under similar synthesis condition, polyaniline in the emeraldine oxidation state shows higher molecular weight compared to leucomeraldine oxidation state. This difference is molecular weight is attributed to bigger hydrodynamic radius of polyaniline in the emeraldine oxidation state due to rod-like chain conformation, while polyaniline in the leucoemeraldine oxidation state has comparatively smaller hydrodynamic radius due to its flexible coil like chain conformation. Therefore, a change in oxidation state or doping level will disrupt the polymer chain stacking of polyaniline of a specific morphology thereby changing the porosity of structure. Thus, a polyaniline-based POHR of the present invention containing an encapsulant such as a corrosion inhibitor will effectively release its encapsulant on change in pH, electrochemical potential, or voltage.

Also, with pH change, release of encapsulants is observed, which can be attributed to a change in molecular chain conformation of polyaniline due to doping/de-doping redox chemistry occurring on the polymer chain. For example, POHR in its doped (conducting form) releases the encapsulant under high pH conditions while the POHR in its base (de-doped, insulating form) release its encapsulant on under low pH condition.

(F) Application of POHR Comprising Encapsulants

The stimuli-responsive micro-reservoirs (POHR) of the present invention can be used in a variety of applications, for example:
1. self-healing corrosion inhibiting additives and self-healing anticorrosive coatings matrix comprising such additives;
2. lubricant additives and lubricant matrix comprising such additives;
3. adhesive additives and adhesive matrix comprising such additives;
4. biocide and Antifouling (B &A) additive and B & A matrix comprising such additive;
5. pesticide additive and pesticide matrix comprising such additive;
6. drug delivery additive and drug delivery matrix comprising such additive;
7. corrosion sensor additive and corrosion sensor matrix comprising such additive;
8. fragrance releasing additive and fragrance releasing matrix comprising such additive;
9. catalyst additive and catalyst matrix comprising such additive;
10. ink additive and ink matrix comprising such additive;
11. dye additive and matrix comprising such additive;
12. an enzyme additive and a matrix comprising such additive; and
13. a reactant additive and a matrix comprising such additive.

In the above examples, by "matrix" is meant the medium in which such POHR comprising encapsulants are dispersed. The examples of such "matrix" include: paints and coatings to which POHR comprising corrosion inhibitor are added; lubricant oil such as motor oil to which POHR comprising lubricant additives are added; an adhesive such as epoxy or urethane adhesive to which POHR comprising adhesive additive are added, and so on, and so forth. The matrix can be a fluid, solid, semi-solid, gel, sol-gel, dispersion, emulsion, a colloidal suspension, gas-liquid mixture, paste, polymeric matrix, or other such combinations that are amenable to such POHR micro-reservoirs. It is possible that when the POHR are added to the matrix the matrix is in one physical and chemical form, and later on, it changes to another physical and/or chemical form.

(a) Self-Healing Corrosion-Inhibiting Additive and Anti-Corrosive Coating Matrix Comprising the Additive To protect metal surface from corrosion and other damages, coatings are applied onto the metal surface. Corrosion inhibitors are added to coatings to slow down or inhibit metal corrosion. The industry standard or incorporating a corrosion inhibitor into a coating is by direct addition. Even though this method is straight forward, the inhibitor may not be directly exposed upon damage to coating, limiting its effectiveness. Also, over time, due to rain, moisture and other environmental factors, the corrosion inhibitor may leach out from the coatings surface and decrease the coating's corrosion inhibition efficiency. Also, conventional coatings fail to provide controllable release, on demand, of the active agents in response to damage, neither exactly at the damaged site of the coating, and nor in the amount needed to correct or completely eliminate damage. Therefore, a stimuli-sensitive coating comprising capsule or reservoirs of corrosion inhibitors that have ability to release the corrosion inhibitor on-demand at the site of the corrosion-induced damage of the coating will increase the corrosion inhibition life and efficiency of coating.

The POHR of the present invention can be used in industries such as oil and gas, automotive, chemical plants, marine, and construction such as buildings, facilities, and industrial facilities, infrastructure such as roads, railings, bridges, tracks, architecture, containers, industrial applications, cladding, decorative, petrochemicals, power generation facilities, water and sewage, municipal, works, and even high-end manufacturing facilities such as clean technology manufacturing. The POHR would be particularly useful in coatings that cover hard-to-reach places that are likely to be ignored for generalized lack of access.

To improve the corrosion-inhibition longevity of coating, the corrosion inhibitor should be preserved for a longer time in the coating and should be made readily and/or immediately available at the corroding site if there is a scratch or mechanical damage on the surface. The corrosion-inhibitor-comprising micro-reservoirs in the anticorrosive coating not only prevent corrosion of metal generally, but heal and protect the metal from further corrosion in case of scratch or mechanical damage on the surface by rapidly arresting the corrosion.

The corrosion inhibitor to be stored in the microreservoirs of the present invention maybe any corrosion inhibitor known in the prior art which is suitable for the intended purpose. The choice of corrosion inhibitor will depend upon the nature of metal and the metallic structure to be protected, environmental conditions, operating conditions, etc.

A partially-open, hollow reservoir that can release encapsulated corrosion inhibitor, actually at the onset of corrosion would be of great benefit.

Because the reservoirs of the present invention are sensitive to electrochemical reduction and corrosion is an oxidation process, reservoir encapsulated with corrosion inhibitor when added as additive in the coating, releases the corrosion inhibitor directly at the corroding site and specifically at the onset of corrosion, thereby self-healing, and protecting the metal from corrosion.

Corrosion inhibitors encapsulated in POHR reservoirs are selected from one of more of the following groups:

(i) an organic compound containing an amino group or carboxy group or salts of carboxylic acids, azoles like imidazoles, thiazoles, tetrazoles, and triazoles like (substituted) benzotriazole, and 2-mercaptobenzothiazole; amines like N-phenyl-1.4-phenylenediamine and Schiff bases (condensation products of amine with aldehyde or ketone) such as N,N'-o-phenylen-bis (3-methoxysalicylidenimine); amino acids like tryptophan thiole group compounds such as DMTD or 1-phenyl-2.5-dithiohydrazodicarbonamide; phthalazin derivatives like 2-[(7-anilino-5-[1,2,4] triazolo[3, 4-b][1,3,4]thiadiazin-3-yl) methyl] phthalazin-1(2H)-one; tannins and substituted uracils; phosphonic acid group-containing materials such as styrenephosphonic acid; succinic acid; (benzothiazol-2-ylthio) succinic acid; fatty acid derivatives such as linoleic acid and TEOA; tallow oil fatty acid salts; and sulphonates, pyridinium group, pyrazine group, an azole derivative quinoline and quinolone compounds;

(ii) an organic compound containing one or more anions selected from the group comprising polyphosphate and its derivatives, nitrite, silicate, molybdate, and polymolybdate and its derivatives, vanadate and polyvanadate and its derivatives; and, (iii) an organic or inorganic compound comprising one or more cations selected from the group comprising lanthanides, magnesium, calcium, titanium, zirconium, yttrium, chromium and silver.

The reservoir encapsulated with corrosion inhibitor may be added to a matrix such as pre-treatments, that is, initial binding layer on metal substrates, conversion coatings, primers, formulations of polymer coatings, powder coatings, paints and concrete, in particular in the form of a powder or a suspension.

Corrosion inhibition can be achieved on various metals, such as iron, copper, zinc, and alloys such as steel. Other exemplary metals and metal alloys for corrosion protection using the present invention include aluminum, zinc, magnesium alloys, zinc alloys, copper alloys, and brass. The application fields of the present invention include automotive, aerospace, construction, architecture, transportation, marine, coil, decorative, cladding, etc. That is, the present invention can be used on any object likely to undergo corrosion.

The micro-reservoir additive may be used in aqueous based, solvent based and powder based coatings.

(b) Lubricant Additives and Lubricant Matrix Comprising the Additive

Lubricants are used in applications that typically involve moving metal parts. They reduce the friction generated between moving parts due to wear and heating, for example. Because lubricants also coat metal parts, they help inhibit corrosion. Functional additives are added into lubricants to increase the performance. For example, a lubricant may include antioxidant additives that prevent the oil from thickening; friction modifier additives that increase engine efficiency; dispersant additives that hold contaminants in suspension; antifoam additives that inhibit the production and retention of air bubbles; detergent additives that reduce deposits on metal; and corrosion inhibiting additives to inhibit corrosion of metals.

Encapsulating additives in reservoirs preserves them in the lubricant for a longer time, and provides several benefits such as:

i. Timed release of the chemical additive for long term protection;
ii. Reduce effective dosage of additive by avoiding deleterious additive-additive interaction;
iii. Deliver the desired chemistry at the right time and the right place to achieve performance not possible when added additive directly;
iv. increase lubricant efficiency by delivering the correct amount of additive for maximum effect;
v. Reduce waste by increasing the effective dosage of additive to be delivered, consequently lowering cost and providing environmental benefits (e.g., less waste oil going into the environment);
vi. Allow the introduction of biodegradable agents to accelerate the safe and rapid decomposition of waste lubricants.

Lubricant additives that may be encapsulated in reservoir also include antioxidant additives belonging to the class of phenols and its derivatives, aromatic and aryl amines, anti-wear additives belonging to the class of metal alkyltiophosphate, dispersants belonging to class of phenates, sulfurized phenates, salicylates, naphthenates, stearates, carbamates, thiocarbamates, phosphorous derivatives, etc.

(c) Adhesive Additives and Adhesive Matrix Comprising Such Additives

This invention also relates to POHR based additives used in adhesives. Adhesives can be gels, pastes, liquids, or any other matrix form. Some examples of adhesives include urethane and epoxy based systems. Adhesives can be thermosetting resin based or thermoplastic based materials. Polymeric gels also are adhesive materials that can be used as matrix in conjunction with the POHR of the present invention.

For example, in electronic devices, conductive elements may be bonded to one another by means of adhesives. In many industries, manufacturers of metal components use structural adhesives to replace conventional fastening techniques such as rivets, bolts, and welding. Adhesives provide improved product performance, aesthetics, reduced overall assembly time, and lower production costs. Additionally, adhesives preclude much of the stress point concentration, corrosion, and component damage often seen with rivets, bolts, welding, and other traditional fastening methodologies.

This invention also relates to using adhesives comprising the POHR in attaching two different types of materials together, e.g., in automotive applications, in order to reduce the overall weight of the structure. For example, in automotive, the inner and outdoor panels, hoods and deck lids can be made of any combination of steel panels, aluminum panels, magnesium alloy panels, copper alloy panels, carbon composite to satisfy structural, weight and appearance requirements.

However, combination of metals (adjacency) increases susceptibility to corrosion because closely spaced metal structures are likely to generate to galvanic action between them.

Therefore, an adhesive composition comprising micro-reservoirs encapsulated with corrosion inhibitor of the present invention effectively inhibits corrosion when two different types of metal are bonded together. The corrosion inhibitor is released when: (i) the POHR is mechanically shattered at the time when two metal pieces are pressed together for bonding; (ii) a corrosion event occurs; and/or (iii) is released gradually from the POHR after the completion of the adhesive bonding process, and during the life of bonded assembly.

The examples of corrosion inhibitors may include chromate compositions or phosphates, silicates, nitrates, benzoates, for protecting aluminum alloy or magnesium alloy, mercaptobenzothiazoles for copper alloys, sodium molybdate formulations for ferrous alloys, and phosphonic acids combined with amines for steel.

In one embodiment, for an adhesive application, the POHR is an integral part of the control of reaction and curing processes. A curing agent is encapsulated into the POHR and added to adhesives. After applying the adhesive to a screw, for example, the screw tightening action bursts the POHR in between the threads, releasing active materials, which initiate the cure.

In one embodiment, the micro-reservoirs act as spacers; including them in an adhesive results in a predetermined minimum bond-line thickness between two substrates.

(d) Biocide and Anti-Fouling (B & A) Additive and Matrix Comprising Such Additive Marine coatings and paint manufacturers customarily add biocides to the paint to prevent or inhibit unwanted infestation of the films by microorganisms, for example, fungi such as molds and yeasts; bacteria; algae; and cyanobacteria (so-called "soft fouling") when these paints are applied on a vessel or underwater structure such as a pier.

The B & A additives have also been effective in some cases in preventing the growth of barnacles, tube worms, and the like (so-called "hard fouling"). However, poor control of biocides release is the main drawback of these systems. Most coatings suffer from premature leakage of biocides, reducing its antifouling action before the end of coatings' lifetime. Alternatively, higher biocide content can be used to reach the required lifecycle, but the continued releasing of those toxic agents into the environment seriously harms the ecosystem, owing to the ecotoxicity and cumulative effect of the applied bioactive agents. Rigid international regulations have been issued as a matter of consequence. Therefore, ability to store biocides or antifoulants in coating for a longer time and its controlled release in coatings over time is of significant importance.

Because the POHR of the present invention have one or more openings on its surface, and the stimuli is chemical/electro-chemical, and/or mechanical, a release profile can be structured according to the need, as described elsewhere in this application. For example, a continuous release, or a timed release, or a slow release can be tailored according to expectation. This invention also relates to using multiple biocides in one POHR or one biocide per set of POHR in plurality of POHR sets. Suitable biocides may include Triazoles, imidazoles, succinates, benzamides, iodine, phenol, pyridine, quinoline, nitrides, phosphates and their respective derivatives. In one embodiment, suitable biocides can be one or more of an inorganic, organometallic, metal-organic or organic biocide for marine or freshwater organisms.

Examples of inorganic biocides include copper salts such as copper oxide, copper thiocyanate, copper bronze, copper carbonate, copper chloride, copper nickel alloys, and silver salts such as silver chloride or nitrate.

Examples organometallic and metal-organic biocides include zinc pyrithione (the zinc salt of 2-pyridinethiol-1-oxide), copper pyrithione, bis (N-cyclohexyl-diazenium dioxy) copper, zinc ethylene-bis(dithiocarbamate) (i.e. zineb), zinc dimethyl dithiocarbamate (ziram), and manganese ethylene-bis(dithiocarbamate) complexed with zinc salt (i.e. mancozeb).

Examples of organic biocides include formaldehyde, dodecylguanidine monohydrochloride, thiabendazole, N trihalomethyl thiophthalimides, trihalomethyl thiosulphamides, N-aryl maleimides such as N-(2,4,6-trichlorophenyl) maleimide, 3-(3,4-dichlorophenyl) 1,1-dimethylurea (diuron), 2,3,5,6-tetrachloro-4-(methylsulphonyl) pyridine, 2 methylthio-4-butylamino-6-cyclopopylamino-s-triazine, 3-benzo[b]thien-yl-5,6 dihydro-1,4,2-oxathiazine 4-oxide, 4,5-dichloro-2-(n-octyl)-3(2H)-isothiazolone, 2,4,5,6-tetra-chloroisophthalonitrile, tolylfluanid, dichlofluanid, diiodomethyl-p tosylsulphone, capsciacin, N-cyclopropyl-N'-(1,1-dimethylethyl)-6-(methylthio)-1,3,5-triazine-2,4-diamine, 3-iodo-2-propynylbutyl carbamate, medetomidine, 1,4-dithiaanthraquinone-2,3-dicarbonitrile (dithianon), boranes such as pyridine triphenylborane, a 2-trihalogenomethyl-3-halogeno-4-cyano pyrrole derivative substituted in position 5 and optionally in position 1, such as 2-(p-chlorophenyl) 3-cyano-4-bromo-5-trifluoromethyl pyrrole (tralopyril), and a furanone, such as 3-butyl-5-(dibromom-ethylidene)-2(5H)-furanone, and mixtures thereof, macrocyclic lactones such as avermectins, for example avermectin B1, ivermectin, doramectin, abamectin, amamectin and selamectin, and quaternary ammonium salts such as didecyldimethylammonium chloride and an alkyldimethylbenzylammonium chloride.

(e) Pesticide Additive and Pesticide Matrix Comprising Such Additive

Pesticides are undoubtedly critical elements of modern agricultural production. They can effectively increase crop yield by reducing plants pests and diseases. However, the traditional pesticide formulations have several disadvantages such as high organic solvent contents, dust drift, poor dispersibility and most importantly most of the pesticide is lost to the environment and less than 1% remains on the target. This low effectiveness contributes to serious environmental pollution associated with pesticides. Therefore, efforts should be taken to reduce waste, production cost and environmental pollution associated with pesticides while also extending the duration of pesticide activity on crops.

One of the methods to address these challenges would be by using precise controlled release of pesticides, an aspect of the present invention. This approach aims to minimize the crop's demand for pesticides to gradually achieve more effective, safe pesticide usage through smart design that slows and controls pesticide release.

Also, in addition to slow release of pesticides, if a system allows responsive release of pesticides in response to light, temperature, soil pH, humidity etc., it is possible to greatly improve use of pesticides by reducing waste and pollution.

The POHR pf the present invention encapsulated with pesticide, achieve a controlled pesticide release and also enables pesticide release in response to change in pH, which improves the pesticide use by reducing waste and pollution.

Examples of pesticides amenable to the POHR encapsulation of the present invention include pyrethroids such as bifenthrin, permethrin, deltamethrin, lambda cyhalothrin, cyfluthrin, or betacyfluthrin; organophosphates such as chlorpyrifos; limonoids such as azadirachtin or meliartenin; phenyl pyrazoles or oxadiazines such as indoxacarb; phthalic acid diamides such as flubendiamide and anthranilic diamides, carbamates such as carbaryl (1-naphthyl N-methylcarbamate), neonicotinoids or nitroguanidines such as imidacloprid, thiomethoxam, clothianidin or dinotefuran; diacylhydrazines such as halofenozide; neonicotines such as floconamid; organophosphates such as trichlorfon and pyrazoles such as fipronil.

(f) Drug Delivery Additive and Drug Delivery Matrix Comprising Such Additive

Delivery of drugs or drug precursors to a wound in a timely and controlled manner can provide superior healing by enabling the on-demand release of drugs. The controlled release of drugs can provide more efficient therapy by reducing side effects and enhancing patient compliance. For example, a smart wound dressing can provide superior healing support by enabling the on-demand release of multiple drugs. Smart wound dressings are typically made of stimuli-responsive particles and a controller. There are two different types of stimuli-responsive particles used for drug delivery depending on the source of stimulation factor. If the system responds to local changes in environment, it is called self-regulated or a closed loop system and this normally occurs with enzyme or competitive substances. On the other hand, externally regulated mechanisms governed by outside stimulation forces such as ultrasound, temperature, electric and magnetic fields provide more user control.

The present invention envisions incorporation of pH responsive materials for active delivery in management of chronic wounds. This is a superior alternative because it is not significantly affected by external environmental factors such as temperature. Only severe infection of the chronic wound might change the pH significantly. And such a change can only have a beneficial effect on would through pH based release of drug into the wound without any adverse effect.

Use of an externally regulated stimuli-responsive system enables the immediate treatment and precise release profile control by adjusting the rate and dosage, externally.

The POHR of the present invention encapsulated with a drug achieve both externally regulated drug delivery and drug delivery in response to change in local environment.

Examples of antibiotic drugs include tetracycline, penicillins, terramycins, erythromycin, bacitracin, neomycin, polymycin B, mupirocin, clindamycin and mixtures thereof. Preferred antiseptics include silver sulfadiazine, chlorhexidine, povidone iodine, triclosan, other silver salts, sucralfate, quaternary ammonium salts and mixtures thereof. These drugs are encapsulated and released upon change in pH.

(g) Corrosion Sensor Additive and Corrosion Sensor Matrix Comprising Such Additive Anticorrosive coatings are frequently used for corrosion prevention of metallic structures and they are often able to delay the corrosion process but not completely prevent it.

Therefore, it is essential to detect corrosion when it occurs, and preferably at its early stage, so that action can be taken to avoid structural damage or loss of function of metals and their alloys. Corrosion sensing coatings are highly desired for corrosion control, especially if the signal can be detected through visual inspection by the naked eye, at a stage much earlier than the appearance of the observable corrosion products.

The POHR of the present invention encapsulated with a dye moiety achieves the release of dye in response to corrosion due to change in pH, thereby signaling the event of corrosion directly to the naked eye.

(h) Fragrance Releasing Additive and Fragrance Releasing Matrix Comprising Such Additive Compositions incorporating one or more sensory markers in the form of a perfume provide a perceived benefit to consumers in that articles treated with the compositions are more aesthetically pleasing to the consumer, including cases where the perfume imparts a pleasant fragrance to the articles treated therewith. One such example is air fresheners. Air fresheners are typical odor modifiers because they employ volatile fragrance agents for odor control by altering a malodor to a more pleasant character or to an acceptable level. Air fresheners were initially used in bathrooms and kitchens and consequently have tended to be more functional than attractive. Air fresheners are now used in bedrooms and living rooms. Thus, an air freshener pack, that slowly releases fragrance over time or a decorative paint that releases fragrance over time would be of significant use.

In one embodiment, the POHR of the present invention encapsulated with a fragrance moiety achieves the sustained release of fragrance over time.

(i) Catalyst Additive and Catalyst Matrix Comprising Such Additive

Encapsulation of catalyst increases the functional life and storage stability of catalyst. Also, encapsulation allows participation of catalyst in a reaction at a desired time thereby increasing the efficiency of reaction.

In order to use encapsulated catalysts in systems that require catalysts, the microcapsules must be rigid enough to withstand processing and remain stable in order not to leak out or release the catalysts prematurely. The microcapsules must be compatible in the systems.

Furthermore, the microcapsules must be able to release the catalysts at the desirable time. Such release mechanisms are needed for certain applications such as in coatings or adhesives in electronic and health care applications. Therefore, there still remains a need for microcapsules encapsulating catalysts that are stable and rigid and easily made compatible, but at the same time able to release the catalysts in a controlled manner.

In one embodiment, the POHR of the present invention that encapsulate a catalyst will release the catalyst through the external stimuli.

In one embodiment one or more additives for ink are dissolved or dispersed in a solvent and are encapsulated in partially-open, hollow reservoirs of the present invention. The POHR comprising the one or more ink additives are mixed with an ink matrix where such additives' functionality is desired. For example, color pigment, or fluorescent, or luminescent pigment, or an adhesive pigment, that is released upon an external stimuli as described herein can be releasably encapsulated in one embodiment of the invention. The ink matrix herein includes printer ink.

In one embodiment one or more additives for of a dye, for example for textile or other coloring applications, are dissolved or dispersed in a solvent and are encapsulated in partially-open, hollow reservoirs of the present invention. The POHR comprising the one or more dye additives are mixed with a dye matrix where such additives' functionality is desired. For example, color pigment, or fluorescent, or luminescent pigment, or an adhesive pigment, that is released upon an external stimuli as described herein can be releasably encapsulated in one embodiment of the invention. For example, textiles can be prepared where a luminescent dye is released to make a fabric look more radiant under certain external stimuli conditions, and that too, in a controlled manner.

In one embodiment one or more additives for an enzyme matrix, for example for use in biological reactions, are dissolved or dispersed in a solvent and are encapsulated in partially-open, hollow reservoirs of the present invention. The POHR comprising the one or more enzyme additives are mixed with an enzyme matrix where such additives' functionality is desired. For example, enzyme that is released upon an external stimuli as described herein can be releasably encapsulated in one embodiment of the invention. For example, reactions can be enzymatically catalyzed using the POHR comprising enzyme of the present invention, using certain external stimuli conditions described herein in this disclosure, and that too, in a controlled manner.

In one embodiment one or more additives for a reaction matrix, for example for use in micro-reactions, are dissolved or dispersed in a solvent and are encapsulated in partially-open, hollow reservoirs of the present invention. The POHR comprising the one or more enzyme additives are mixed with a reaction mixture where such additives' functionality is desired. For example, reactant that is released upon an external stimuli as described herein can be releasably encapsulated in one embodiment of the invention. For example, chemical equilibrium of micro-reactions can be changed by changing the concentration of a particular reactant by using the POHR comprising the reactant of the present invention, by employing certain external stimuli conditions, and that too, in a controlled manner.

VI. EXPERIMENTAL

I. Preparation of POHR

This set of experiments describes various methods of preparing the POHR.

Example 1.1: Synthesis of Poly-o-toluidine Partially-Open, Hollow Reservoirs In this example, o-toluidine monomer (0.12 M) was oxidatively polymerized in 400 ml of water using ammonium peroxydisulfate oxidant (0.12 M) under controlled temperature conditions (5-10° C.).

Figure 3:
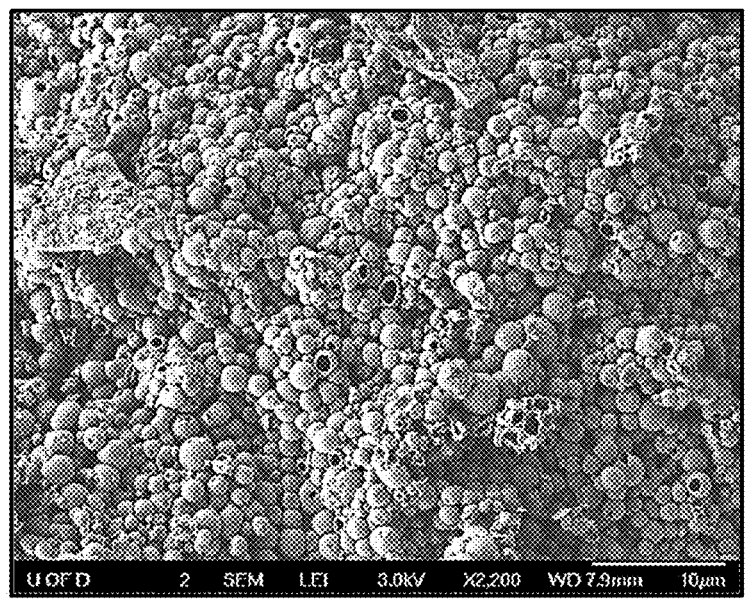
FIG. 3: SEM image of poly-o-toludine (POT) micro-reservoirs.

In the first step, the monomer o-toludine (0.24 M) was dissolved in 200 ml water in a first beaker, with stirring. In a second beaker, ammonium peroxydisulate (0.24 M) was dissolved in 200 ml water, with stirring. Both beakers were placed in an ice-bath until the temperature of the components in the two beakers reached from 5-10° C. Then, the ammonium peroxydisulfate solution was added to the monomer solution, with stirring. After about 2 min, the stirring was stopped and the reaction was left undisturbed in ice-bath for 8 hours. The reaction mixture was then filtered and was washed with copious amounts of de-ionized water. This step was followed by washing with ethanol—to remove oligomeric impurities—until the filtrate was rendered almost colorless. The polymer obtained was dried in oven at 70° C. FIG. 3 is a scanning electron micrograph of the partially-open, hollow reservoirs obtained from this experiment.

Example 1.2: Synthesis of Poly-o-methoxyaniline POHR

In this example, o-methoxyaniline monomer (0.18 M) was oxidatively polymerized in 400 ml of water using ammonium peroxydisulfate oxidant (0.18 M) under controlled temperature conditions (0-5° C.).

Figure 4:
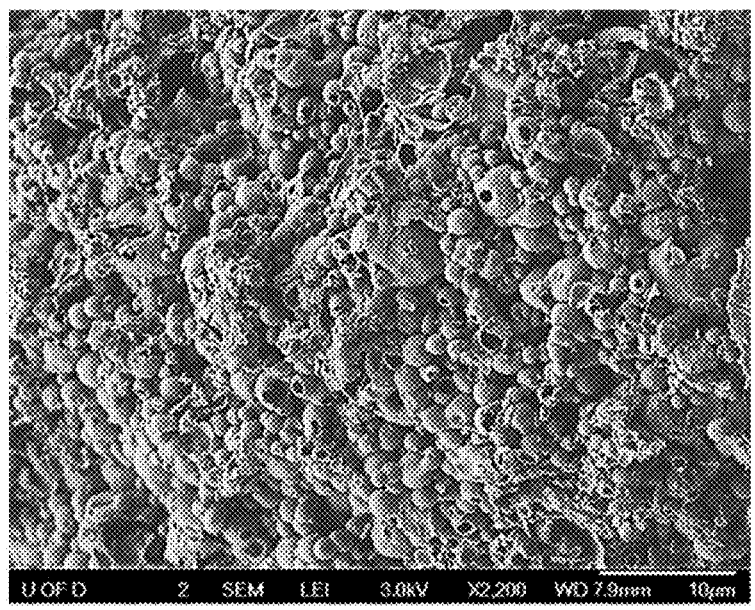
FIG. 4: SEM image of poly-o-methoxyaniline micro-reservoirs.

In the first step, the o-methoxyaniline monomer (0.36 M) was dissolved in 200 ml water in a first beaker, with stirring. In a second beaker, ammonium peroxydisulate (0.36 M) was dissolved in 200 ml water, with stirring. Both beakers were placed in an ice-bath until the temperature reached 0-5° C. Then, the ammonium peroxydisulfate solution was added to the monomer solution with stirring. After about 2 min, the stirring was stopped and the reaction was left undisturbed in ice-bath for 8 hours. The reaction mixture was then filtered and was washed with copious amounts of de-ionized water. This was followed by washing with ethanol—to remove oligomeric impurities—until the filtrate was rendered almost colorless. The polymer obtained was dried in oven at 70° C. FIG. 4 is a scanning electron micrograph of the partially open, hollow reservoirs obtained from this experiment.

Example 1.3: Synthesis of Polyaniline Nanotube Reservoirs (N-POHR)

Figure 5:
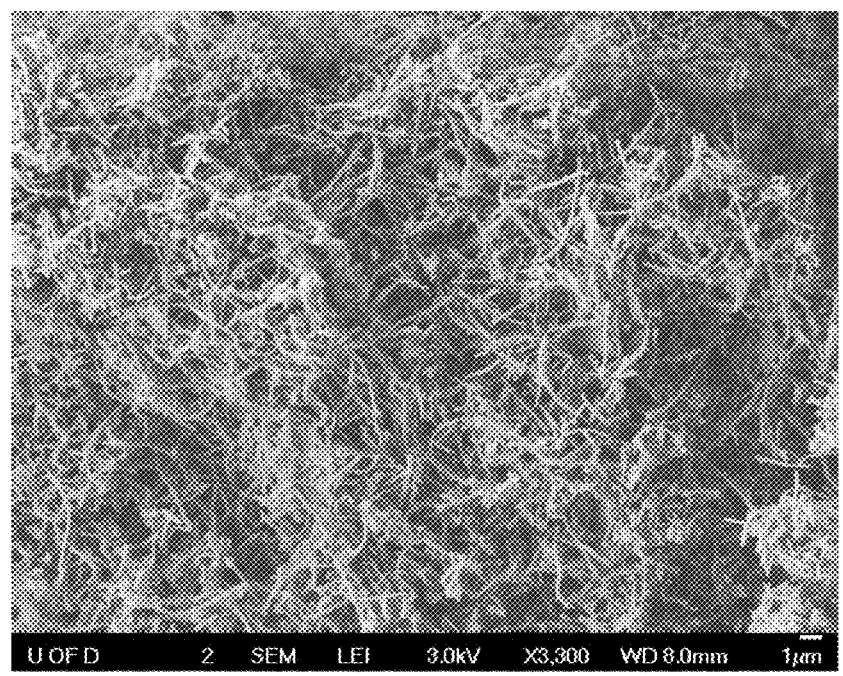
FIG. 5: SEM image of polyaniline nanotubes reservoirs.

In a first beaker, a solution of lactic acid (0.032 M) was prepared in 500 ml water. Aniline (0.065 M) was added to the lactic acid solution, with stirring. In a second beaker, ammonium peroxydisulfate solution (0.065 M) was prepared in 500 ml of water. The ammonium peroxydisulfate solution was added to aniline/lactic acid solution and the reaction was left undisturbed for 12 hours, at room temperature. The reaction mixture was then filtered and was washed with copious amounts of de-ionized water. This step was followed by washing with ethanol—to remove oligomeric impurities—until the filtrate was rendered almost colorless. The polymer obtained was dried in oven at about 70° C. FIG. 5 is a scanning electron micrograph of the partially-open, hollow reservoirs obtained from this experiment.

Example 1.4: Synthesis of Poly-o-toluidine Partially-Open, Hollow Reservoirs with Multiple Openings on its Surface In this example, o-toluidine monomer (0.24 M) was oxidatively polymerized in 400 ml of water using ammonium peroxydisulfate oxidant (0.24 M) under controlled temperature conditions (5-10° C.).

Figure 6:
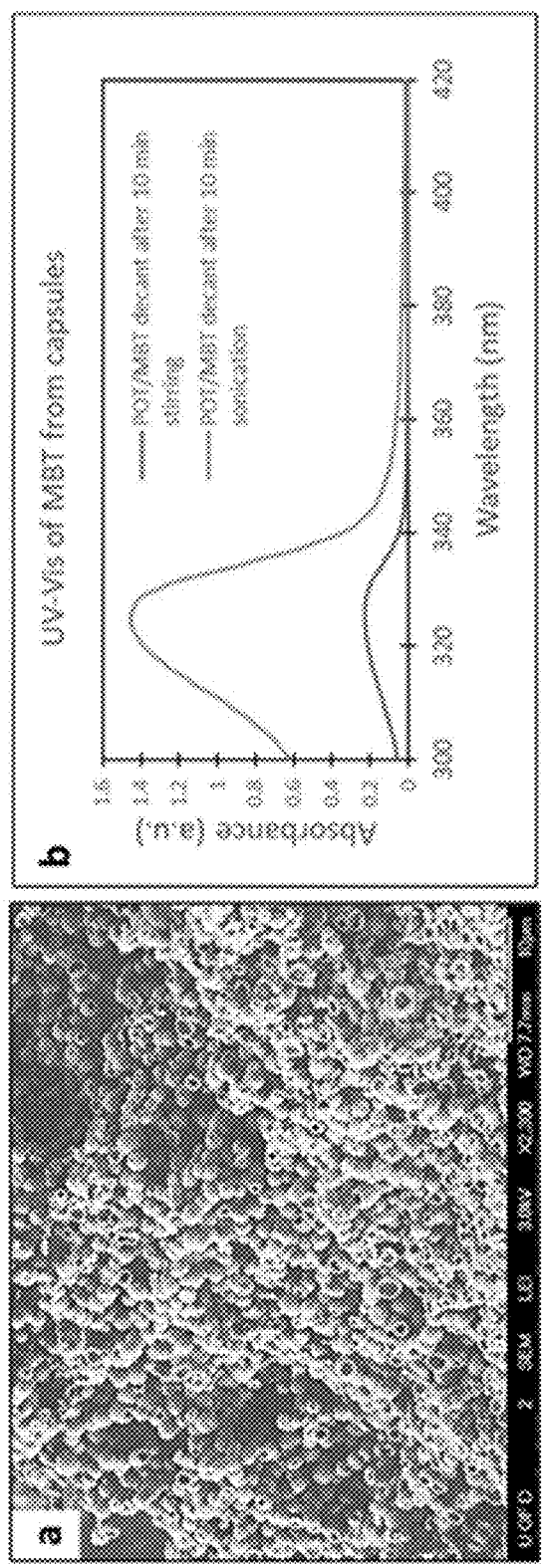
FIG. 6: (a) SEM image of the poly-o-toluidine micro-reservoirs encapsulated with mercaptobenzothiazole (MBT); (b) UV-Vis analysis to confirm MBT is encapsulated inside poly-o-toluidine.

In the first step, the monomer o-toludine (0.48M) was dissolved in 200 ml water in a first beaker, with stirring. In a second beaker, ammonium peroxydisulate (0.48 M) was dissolved in 200 ml water, with stirring. Both beakers were placed in an ice-bath until the temperature of the components in the two beakers reached from 5-10° C. Then, the ammonium peroxydisulfate solution was added to the monomer solution, with stirring. After about 2 min, the stirring was stopped and the reaction was left on a vibrating surface in ice-bath for 8 hours. The reaction mixture was then filtered and was washed with copious amounts of de-ionized water. This step was followed by washing with ethanol—to remove oligomeric impurities—until the filtrate was rendered almost colorless. The polymer obtained was dried in oven at 70° C. FIG. 6 is a scanning electron micrograph of the partially-open, hollow reservoirs obtained from this experiment.

II. Encapsulation of Encapsulants Inside POHR

This set of experiments describes various methods of encapsulating an encapsulant inside a POHR.

Example 2.1: Encapsulation—Solvent-Evaporation Method—Mercaptobenzothiazole Encapsulant in Poly-o-toluidine-Based POHR General Procedure In the solvent-evaporation method, a saturated solution of encapsulant is prepared in a solvent (for example, ethanol) in the first step. In the next step, partially-open, hollow reservoirs (POHR) are dispersed in this encapsulant/solvent (for example, ethanol) solution, with stirring. Because the reservoirs are hollow with at least one opening on their surface, the encapsulant and solvent (for example, ethanol) seeps in the interior of the hollow reservoirs. After 2 hours of stirring, the solvent (for example, ethanol) is evaporated under vacuum, with stirring, such that the encapsulant is encapsulated inside the reservoir. After evaporating the solvent (for example, ethanol), the POHR/encapsulant product is quickly washed with solvent (for example, ethanol) to remove any encapsulant precipitated on the surface of the capsule. The product is then dried in an oven at a temperature amenable to the solvent being used, for example, 70° C., for ethanol.

More specifically, a saturated solution of mercaptobenzothiazole (MBT), a corrosion inhibitor was prepared by dissolving 2 g of MBT in 100 ml ethanol. Polyaniline-based POHR, specifically, poly-o-toluidine (POT) reservoirs, 2 g, were dispersed in this MBT/ethanol solution with stirring. Because the reservoirs are hollow with at least one opening on their surface, it is speculated that MBT and ethanol seeped into the interior of the hollow reservoirs. After 2 hours of stirring, ethanol was evaporated under vacuum with stirring, at 60° C., such that the MBT was encapsulated inside the reservoir. After evaporating the ethanol, the POT-POHR/MBT product was quickly washed with ethanol to remove any corrosion inhibitor precipitated on the surface of the POHR. The product was then dried in oven at 70° C.

As shown in the SEM image in FIG. 6a, the process of encapsulating the MBT inside the POHR did not destroy or damage the reservoirs, at all, or in any substantial manner, indicating the reservoirs were indeed robust.

To confirm that the corrosion inhibitor—MBT—indeed was encapsulated inside the reservoirs, a UV-Vis analysis of the POHR encapsulating the MBT was performed.

Reservoirs comprising the MBT encapsulant were dispersed in water, with stirring, for 10 min and were then subjected to centrifugation. The decant was tested for the presence of corrosion inhibitor. Subsequently, the same reservoirs were re-dispersed in water but were additionally bath-sonicated for 10 min to break them and remove the encapsulant from their interior.

The sonicated reservoirs were centrifuged and the UV-Vis absorbance of the decant was measured. As shown in FIG. 6b, after sonication, the concentration of corrosion inhibitor increased in the decant—as indicated by almost a 10× increase in the Absorbance units at a specific wavelength—indicating the release of corrosion inhibitor from inside the reservoirs upon their breakage, which leads one to conclude that the corrosion inhibitor indeed was residing in the interior of the POHR.

Example 2.2: Encapsulation—The In-Situ Deposition Method—Triethanolamine (TEA) Encapsulant in Poly-o-toluidine-Based POHR The in-situ deposition method was used when hydrophilic and/or water-soluble moieties were to be encapsulated inside the partially-open, hollow reservoirs (POHR) during synthesis of these reservoirs. In a typical procedure, first, the encapsulant was dissolved in water. Then, the monomer was polymerized in presence of the dissolved encapsulant.

More specifically, in a first beaker, 2.98 g triethanolamine (TEA) was dissolved in 100 ml of water. In this solution, 3.94 g of o-toluidine monomer was added, with stirring.

In a second beaker, 7.3 g ammonium peroxydisulfate was dissolved in 100 ml of water. Both beakers were placed in an ice-bath until the temperature reached 5-10° C.

Then, the ammonium peroxydisulfate solution from the second beaker was added to the monomer/TEA solution in the first beaker, with stirring.

After about 2 min, the stirring was stopped and the reaction was left undisturbed in the ice-bath for 8 hours. The reaction mixture was subsequently filtered and was washed with copious amounts of de-ionized water. This step was followed by washing with ethanol—to remove oligomeric impurities—until the filtrate was almost colorless. The polymer obtained was dried in oven at 70° C.

Figure 7:
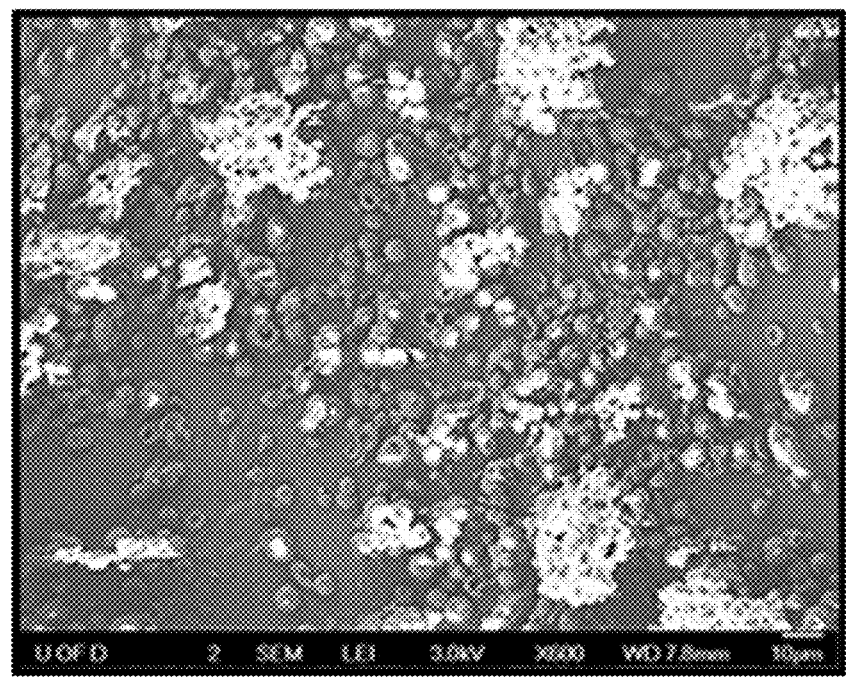
FIG. 7: SEM image of poly-o-toluidine capsules encapsulated with triethanol amine (TEA)

FIG. 7 is the scanning electron micrograph (SEM) of the poly-o-toluidine-based POHR encapsulated with triethanolamine. It is speculated that because both the monomer and triethanolamine are basic in nature—due to charged interaction and hydrogen bonding—TEA stays at the core of the monomer droplet or micelle and gets encapsulated inside the sphere after the polymerization, yielding TEA encapsulated POHR. The charging on the reservoirs during SEM imaging indicates the presence of TEA inside and on the surface of the reservoirs. Unlike the POHR, the TEA in non-conductive. Consequently, the charge accumulates on surface during SEM imaging, which then shows TEA's presence on the surface of the POHR.

Example 2.3: Encapsulation—The Precipitation Method—Halox 570 Encapsulant in Poly-o-toluidine-Based POHR General Procedure In the precipitation method, a saturated solution of encapsulant is prepared in a solvent (for example, ethanol) and polymer-based POHR are dispersed in this encapsulant/solvent (for example, ethanol) solution with stirring. Because the reservoirs are hollow with at least one opening on their surface, encapsulant and solvent (for example, ethanol) seep into the interior of the hollow reservoirs. After 2 hours of stirring, solvent (for example, ethanol) is evaporated under vacuum, with stirring, such that the encapsulant is encapsulated inside the reservoir. After evaporating the solvent (for example, ethanol), the POHR/encapsulant product is quickly washed with solvent (for example, ethanol) to remove any encapsulant precipitated on the surface of the POHR. The product is then dried in oven at temperature amenable to the solvent being used, for example, at 70° C. for ethanol.

More specifically, a saturated solution of Halox 570 corrosion inhibitor was prepared by dissolving 10 g of Halox 570 in 100 ml of ethanol. In this Halox 570/ethanol solution, 10 g of POT reservoirs were dispersed, with stirring. Because the reservoirs were hollow with at least one opening on their surface, the corrosion inhibitor and ethanol seeped into the interior of the reservoirs. After 2 hours of stirring, the whole mixture was dumped into ice/cold water such that the corrosion inhibitor precipitated out of ethanol, but on the interior of the hollow reservoirs. The product was filtered, washed with water and dried in an oven at 70° C.

Figure 8:
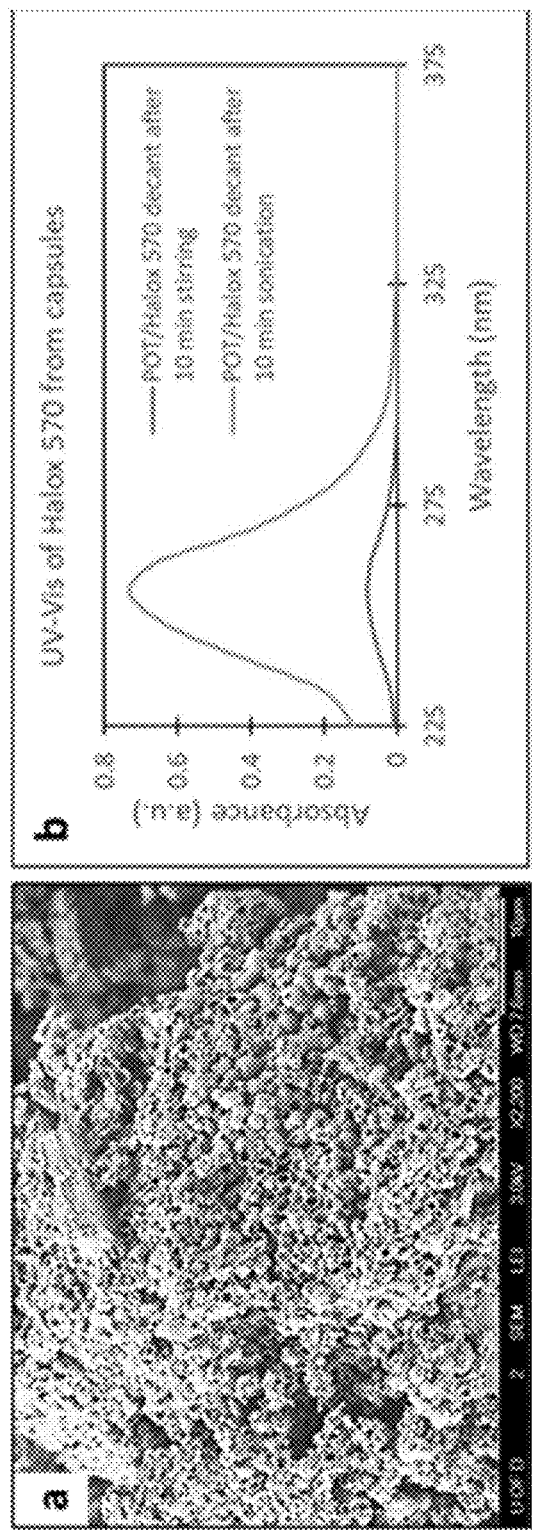
FIG. 8: (a) SEM image of the poly-o-toluidine micro-reservoir encapsulated with Halox 570; (b) UV-Vis analysis to confirm Halox 570 is encapsulated inside poly-o-toluidine.

As shown in the SEM image in FIG. 8a, the process of encapsulating the Halox 570 inside the POHR did not destroy or damage the reservoirs, at all, or in any substantial manner, indicating the reservoirs were indeed robust.

To confirm that the corrosion inhibitor—Halox 570—indeed was encapsulated inside the reservoirs, a UV-Vis analysis of the POHR encapsulating the Halox 570 was performed.

Reservoirs comprising the Halox 570 encapsulant were dispersed in water, with stirring, for 10 min and were then subjected to centrifugation. The decant was tested for the presence of corrosion inhibitor. Subsequently, the same reservoirs were re-dispersed in water but were additionally bath-sonicated for 10 min to break them and remove the encapsulant from their interior.

The sonicated reservoirs were centrifuged and the UV-Vis absorbance of the decant was measured. As shown in FIG. 8b, after sonication, the concentration of corrosion inhibitor increased in the decant—as indicated by almost a 7× increase in the Absorbance units at a specific wavelength—indicating the release of corrosion inhibitor from inside the reservoirs upon their breakage, which leads one to conclude that the corrosion inhibitor indeed was residing in the interior of the POHR.

III. Release of Encapsulants from the Interior of the POHR

This set of experiments describes various methods of releasing an encapsulant from the inside of POHR.

Example 3.1: Release of Encapsulant from Poly-o-Toluidine (POT) POHR Upon Reduction To confirm the release of the encapsulant from reservoirs upon reduction, reservoirs were chemically reduced using hydrazine as the reducing agent.

In the first step, 10 mg of POT reservoirs encapsulated with Halox 570 corrosion inhibitor were dispersed in water. The Halox 570 release from the POHR was monitored, over time, by measuring its Absorbance using UV-Vis spectrometer. As shown in X11, initially the Absorbance of Halox 570 circa 0.25 units, which likely corresponds to a slow, time-based dissipation of the encapsulant from the POHR. As time progressed, Halox 570 release slowed, which is indicated by a positive slope of the Absorbance versus Time plot in FIG. 9.

After 1 hour, a drop of hydrazine was added and Absorbance was measured. It was found that the Absorbance of Halox 570 immediately increased to 1.2 units—a step-change as seen in FIG. 9b—indicating that addition of hydrazine, which means a reduction of POHR triggered an instantaneous release of Halox 570 that had been encapsulated within the interior of the reservoirs. This confirmed that reduction, indeed, triggered the release of encapsulant.

Similar release of encapsulant is observed on change in pH, electrochemical potential, and voltage.

Example 3.2: Release of Encapsulant from Poly-o-Toluidine (POT) POHR Upon pH Change To confirm the release of the encapsulant from reservoirs upon change in pH, reservoirs were immersed in acidic and basic solutions and the release of encapsulant was measured using UV-Vis.

In the first step, 1 g POT-POHR in their conducting (doped) form encapsulated with 2-mercaptobenzothiazole (MBT) was added to each dilute HCl solution of pH~1, DI water of pH~7, and dilute ammonium hydroxide solution of pH~11 and stirred for 5 min. The mixture was filtered and the release of MBT in the filtered solution was analyzed using UV-Vis absorbance spectroscopy. A significant amount of MBT was observed in basic pH solution while no MBT was found in acidic pH solution indicating the release of encapsulant under high pH conditions.

In a second step, 1 g POT POHR in their insulating (base, de-doped) form encapsulated with 2 hydroxybenzoic acid was added to each dilute HCl solution of pH~1, DI water of pH~7, and dilute ammonium hydroxide solution of pH~11 and stirred for 5 min. The mixture was filtered and the release of hydroxybenzoic acid in the filtered solution was analyzed using UV-Vis absorbance spectroscopy. A significant amount of hydroxybenzoic acid was observed in acidic pH solution while very small quantities of hydroxybenzoic acid was found in acidic pH solution indicating the release of encapsulant under low pH conditions. Therefore, release of encapsulant under high pH or low pH conditions can be controlled by using doped or de-doped POHR.

IV. Self-Healing Anticorrosive Coating with POHR Encapsulated Corrosion Inhibitor

Example 4.1: Acrylic Based Anticorrosive Coatings with POT-POHR/Halox 570 Corrosion Inhibitor To test the performance of reservoirs as self-healing anticorrosive coating additive, acrylic-based anticorrosive coatings were formulated with a load of 3 wt. % poly-o-toluidine reservoirs encapsulated with Halox 570 corrosion inhibitor. The performance of the coatings was tested side-by-side with an acrylic-based coating not comprising any corrosion inhibitor and acrylic based coating containing Halox 570 corrosion inhibitor directly added into it.

TABLE 2

Starting Point Formulation for Waterborne Acrylic Coating

| Material Name | Supplier | Amount (g) |
|---|---|---|
| DI Water | | 21.88 |
| Disperbyk 2012 | Evonik | 3.28 |
| Disperbyk 1710 | BYK | 0.54 |
| TiO2 - TiPure R765 | Chemours | 32.82 |
| POT/Halox 570 | SAS Nanotechnologies | 6 |
| Avanse MV 100 | Dow | 131.3 |
| Additol VXW 6360 | Allnex | 0.88 |
| Grind at high speed for 30 min | | |
| Tego Wet 265 | Evonik | 1.76 |
| Dowanol DPM Glycol Ether | Dow | 7.66 |
| Total | | 200 |

The coatings were applied onto cold rolled steel panels as primer, using the drawdown method. The primer coatings were subsequently top-coated with a commercial PittTech® top-coat coating from PPG. The thickness of both the primer and top-coat coatings was about 70 μm each. A scribe was made at the center of the coated panel and was then placed inside a Salt-Fog chamber for accelerated corrosion testing.

The performance of the coated panels was tested using ASTM B117 Salt-Fog Test method. Salt-Fog chamber from Associated Environment Systems was used for testing. The concentration of salt water was 5 wt. %. For control coating samples, all the ingredients were kept the same and in the same quantity, except the control samples did not contain any corrosion inhibitor, encapsulated, or otherwise.

Figure 9:
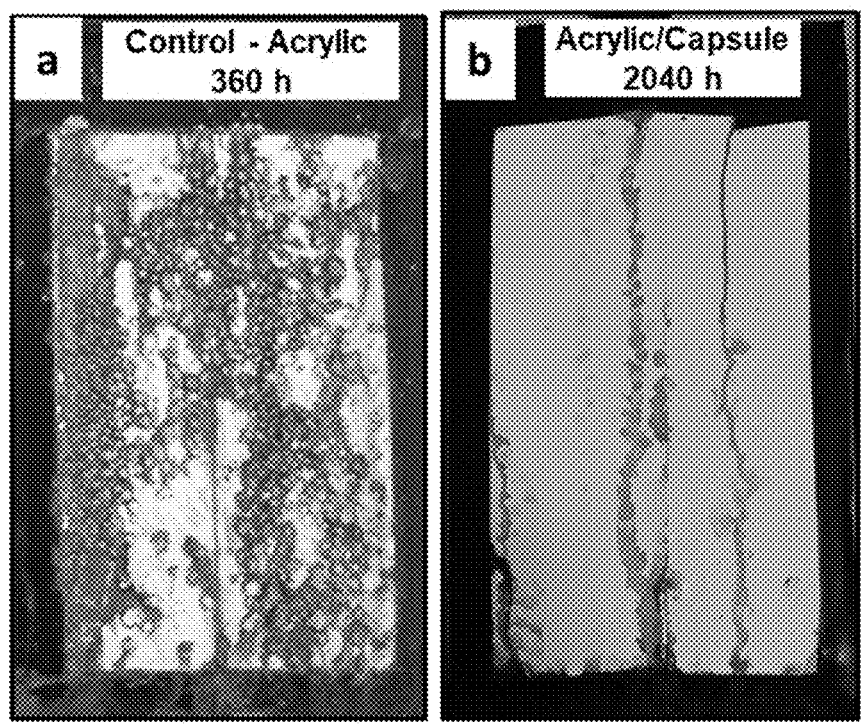
FIG. 9: Digital images of steel panels coated with coatings after ASTM B117 Salt-Fog Test; Primer: (a) Acrylic coating, no micro-reservoirs, control sample, after 360 hours; (b) Acrylic coating containing 3 wt. % POT micro-reservoirs encapsulated with Halox 570, after 2040 hours.

As shown in FIG. 9, coating samples (control) that did not contain reservoirs corroded after 360 hours in the Salt-Fog chamber. In contrast, acrylic coatings formulated with POT reservoirs containing Halox 570 showed excellent corrosion resistance even after 2000 hours of the Salt-Fog Test. Similarly, as shown in FIG. 9.1, coating samples (control) that did not contain reservoirs, corroded after 360 hours in the Salt-Fog chamber. For example, panel that did not contain corrosion inhibitor (FIG. 9.1 a), obviously corroded. However, for middle panel, FIG. 9.1 b, in spite of adding Halox 570 corrosion inhibitor, the panel corroded significantly after 264 hours in the Salt-Fog chamber. In contrast, acrylic coatings formulated with POT reservoirs containing Halox 570 showed excellent corrosion resistance even after 2000 hours of the Salt-Fog Test. This indicates the reservoirs not only preserve corrosion inhibitor for longer time in coating but also show synergistic performance with corrosion inhibitor.

Example 4.2: 2K-Epoxy Based Anticorrosive Coatings with POT-POHR/Halox 570 Corrosion Inhibitor In this example, 2K-molecular weight, -epoxy-based anticorrosive coatings were formulated with a load of 3 wt. % poly-o-toluidine (POT) reservoirs encapsulated with Halox 570 corrosion inhibitor using the encapsulation procedure discussed in Example 4.1 above. The coating performance was also tested. Provided below is the starting point formulation for the coating. The components listed in table below for Part A were mixed using high speed disperser. Part A and Part B were mixed together in 1:1 ratio and applied to a metal substrate.

Figure 10:
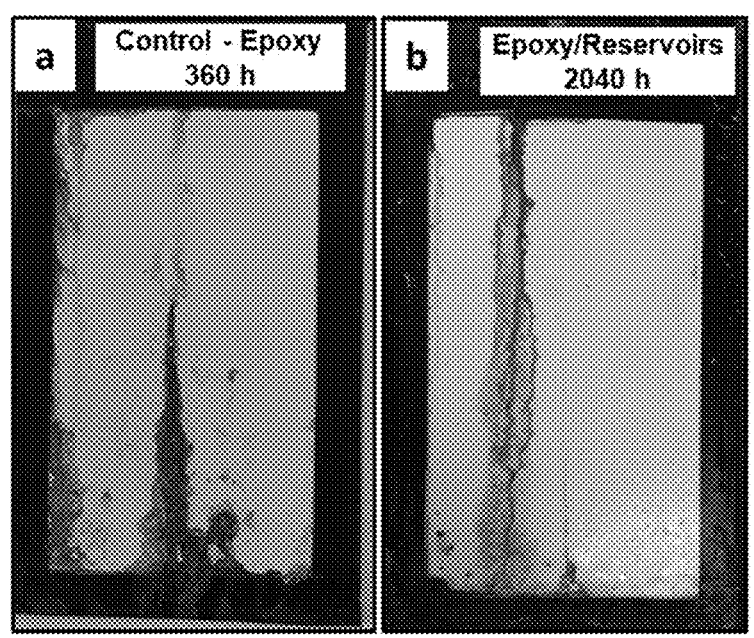
FIG. 10: Digital images of steel panels coated with coatings after ASTM B117 Salt-Fog Test; Primer: (a) 2K-Epoxy coating, no micro-reservoirs, control sample, 360 hours; (b) 2K-Epoxy coating containing 3 wt. % POT reservoirs encapsulated with Halox 570, 2040 hours.

The images of the two panels from the ASTM B117 Salt-Fog Test are shown in FIG. 10. The first panel was coated with control epoxy without the POHR-based corrosion inhibitor. The second panel was coated with the experimental 2K-epoxy coating containing 3 wt. % POT reservoirs encapsulated with Halox 570. The remarkable result is that the POHR based experimental sample showed better corrosion resistance even at 2000 plus hours than the epoxy coating without the POHR, at 360 hours.

TABLE 3

Starting Point Formulation for 2K Epoxy Coating

| Material Name | Supplier | Quantity (g) |
|---|---|---|
| Part A | | |
| Water | | 37 |
| Disperbyk 2012 | BYK | 2.2 |
| Byk 1710 | BYK | 0.22 |
| TiO2 TiPure R765 | Chemours | 37 |
| POT/Halox570 | SAS Nanotechnologies | 6 |
| Aradur 3986 | Huntsman | 23.6 |
| | Total | 125 |
| Part B | | |
| Araldite PZ3961 | Huntsman | 72.24 |
| Water | | 27.76 |
| | Total | 125 |

Example 4.3: Acrylic Based Anticorrosive Coatings with POT-POHR/Halox 570 Corrosion Inhibitor To further understand the corrosion inhibition efficiency of capsules encapsulated with corrosion inhibitor, additional acrylic based control coatings were formulated: (a) a coating with corrosion inhibitor Halox 570 added directly into the coating; (b) a coating with microcapsules or micro-reservoirs devoid of any corrosion inhibitor added into the coating; (c) a coating with microcapsules and corrosion inhibitor Halox 570 added as individual additive into the coating; and (d) a coating with microcapsules encapsulated with Halox 570 corrosion inhibitor.

TABLE 4

Starting Point Formulation for Acrylic Coatings

| Material Name | Supplier | Sample (a) Amount (g) | Sample (b) Amount (g) | Sample (c) Amount (g) | Sample (d) Amount (g) |
|---|---|---|---|---|---|
| DI Water | | 21.88 | 21.88 | 21.88 | 21.88 |
| Disperbyk 2012 | Evonik | 3.28 | 3.28 | 3.28 | 3.28 |
| Disperbyk 1710 | BYK | 0.54 | 0.54 | 0.54 | 0.54 |
| TiO$_2$ - TiPure R765 | Chemours | 32.82 | 32.82 | 32.82 | 32.82 |
| Halox 570 | ICI | 6 | | | |
| POT capsules | SAS Nanotechnologies | | 6 | | |
| POT + Halox 570 | SAS Nanotechnologies | | | 6 | |
| POT encapsulated with Halox 570 | SAS Nanotechnologies | | | | 6 |
| Avanse MV 100 | Dow | 131.3 | 131.3 | 131.3 | 131.3 |
| Additol VXW 6360 | Allnex | 0.88 | 0.88 | 0.88 | 0.88 |
| Grind at high speed for 30 min | | | | | |
| Tego Wet 265 | Evonik | 1.76 | 1.76 | 1.76 | 1.76 |
| Dowanol DPM Glycol Ether | Dow | 7.66 | 7.66 | 7.66 | 7.66 |
| | Total | 200 | 200 | 200 | 200 |

The coatings formulated were applied onto cold-rolled steel panels as primer. The primer coatings were then top-coated with a commercial PittTech® top-coat coating from PPG. The thickness of both the primer and top-coat coatings was circa 70 μm each. The performance of the coated panels was tested using ASTM B117 Salt-Fog Test method. A scribe was made at the center of the coated panel and then placed inside salt fog chamber for accelerated corrosion testing.

Figure 11:
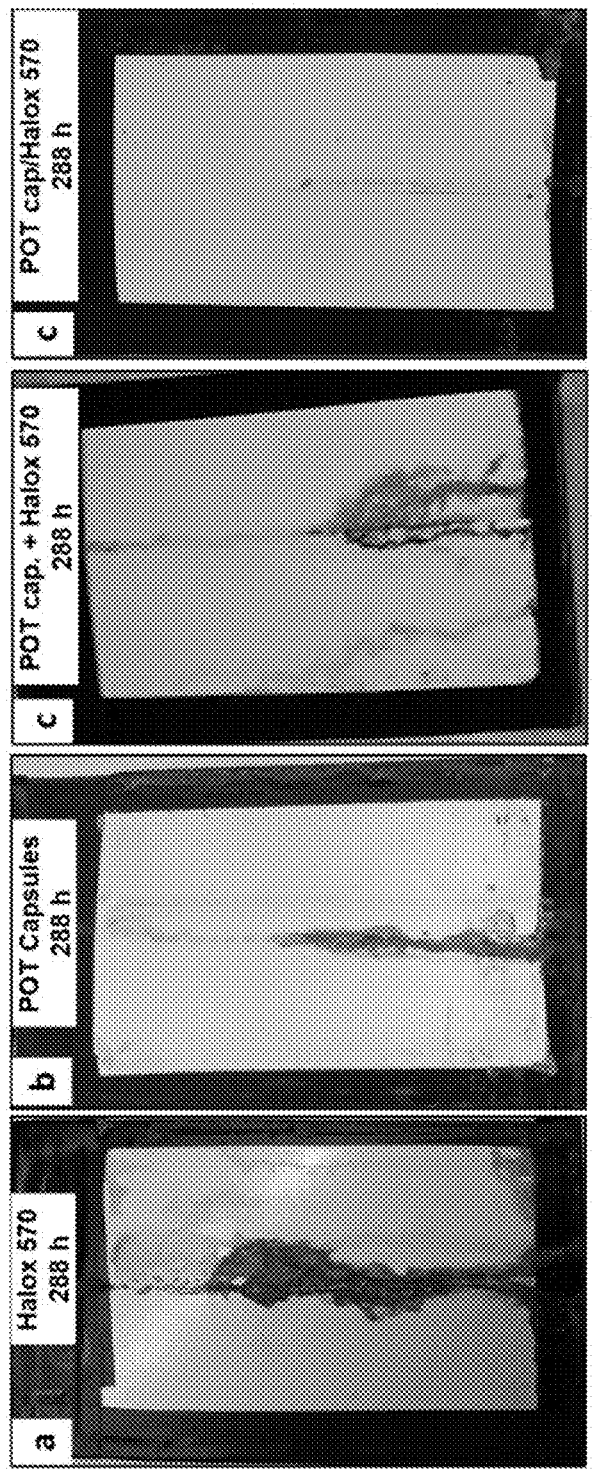
FIG. 11: Digital images of steel panels coated with coatings after ASTM B117 Salt-Fog Test Primer: (a) Acrylic coating containing 3 wt. % Halox 570, 288 hours; (b) Acrylic coating containing 3 wt. % microcapsules but no corrosion inhibitor, 288 hours; (c) Acrylic coating containing 1.5 wt. % microcapsules and un-encapsulated 1.5 wt. % Halox 570, 288 hours; and (d) Acrylic coating containing 3 wt. % microcapsules encapsulated with Halox 570, 288 hours. For all samples, the topcoat was PittTech® PPG coating.

As shown in FIG. 11a below, Halox 570 alone does not have very good corrosion inhibition efficiency. However, coatings based on the microcapsules of the present invention alone (FIG. 11b) show better corrosion inhibition efficiency. This can be attributed to the intrinsic corrosion inhibition property of microcapsules that can prevent corrosion by passivation and by acting as ionic barrier. When a mixture of Halox 570 and microcapsules are added to the coatings, the corrosion inhibition is fair (FIG. 11c). This could be attributed to the leaching of Halox 570 from coating as well as the interference of other coating component with Halox 570 and microcapsules in their function. Halox 570 encapsulated in microcapsules worked the best (FIG. 11d). This is because of the synergistic effect of Halox 570 and microcapsules.

V. Lubricant Additives

Example 5.1: POT Reservoirs Encapsulated with Calcium Sulfonate Corrosion Inhibitor Calcium sulfonates are effective corrosion inhibitors in lubricants and are sold under a variety of brand names. One such brand is Counter Rust™ 7165 from Lockhart. A saturated solution of Counter Rust 7165 (CR) corrosion inhibitor is prepared by dissolving 2 g CR in 100 ml of hexane. Poly-o-toluidine (POT) reservoirs, 2 g, are dispersed in this CR/Hexane solution with stirring. Because the reservoirs are hollow with one or more openings on their surface, CR and hexane seep inside the hollow reservoirs. After 2 hours of stirring, hexane is evaporated under vacuum with stirring at about 60° C., such that the CR is encapsulated inside the reservoir. After evaporating the hexane, the POT reservoir/CR product is quickly washed with hexane to remove any residual CR precipitated on the surface of the reservoir. The product is then dried in oven at 40° C.

The reservoirs encapsulated with corrosion inhibitor are added as additive to the base oil formulation to improve the performance of the lubricant.

Example 5.2: POT Reservoirs Encapsulated with Naphthyl-Phenylamine Antioxidant A saturated solution of 1-Napthyl-phenylamine (NPA) antioxidant is prepared by dissolving 2 g of NPA in 100 ml of ethanol. Poly-o-toluidine (POT) reservoirs, 2 g, are dispersed in this NPA/ethanol solution with stirring. Because the reservoirs are hollow with one or more openings on their surface, NPA and ethanol seep inside the hollow reservoirs. After 2 hours of stirring, ethanol is evaporated under vacuum with stirring at about 60° C., such that the NPA is encapsulated inside the reservoir. After evaporating the ethanol, the POT reservoir/NPA product is quickly washed with ethanol to remove any residual NPA precipitated on the surface of the reservoir. The product is then dried in oven at 70° C.

The reservoirs encapsulated with antioxidant are added as additive to the base oil formulation to improve the performance on lubricant.

Example 5.3: POT Reservoirs Encapsulated with Zinc Dialkyldithiophosphates Antioxidant/Antiwear/Anticorrosion Agents Zinc dialkyldithiophosphates are effective antioxidants, antiwear, and anticorrosion agents in lubricants and are sold under a variety of brand names. One such brand is Additin® RC 3080 from Lanxess and its chemical component is 2-ethyle-hexyl Zinc Dialkyldithiophosphates (EZD). In this example, a saturated solution of Additin® RC 3080 (EZD) additive is prepared by dissolving 2 g EZD in 100 ml water. Poly-o-toluidine (POT) reservoirs, 2 g, are dispersed in this EZD/water solution with stirring. Because the reservoirs are hollow with one or more openings on their surface, EZD and water seep inside the hollow reservoirs. After 2 hours of stirring, water is evaporated under vacuum with stirring at 90° C., such that the EZD is encapsulated inside the reservoir. After evaporating water, the POT reservoir/EZD product is quickly washed with water to remove any EZD precipitated on the surface of the reservoir. The product is then dried in oven at 40° C.

The reservoirs encapsulated with the EZD antiwear agent is added as additive to the base oil formulation to improve the performance on lubricant.

VI. Adhesive Additives

Example 6.1: POT Reservoirs Encapsulated with Aminodiphenylamine Curing Agent In this example, a curing agent, aminodiphenylamine (1 g) is dissolved in 100 ml cyclohexane. Poly-o-toluidine reservoirs, 1 g, are dispersed in aminodiphenylamine/cyclohexane solution with stirring. Because the reservoirs are hollow with one or more openings on their surface, aminodiphenylamine and cyclohexane seep inside POHR. After two hours of stirring, cyclohexane is evaporated under vacuum with stirring at 70° C. such that aminodiphenylamine is encapsulated inside the reservoir. After evaporating the cyclohexane, the POT/aminodiphenylamine product is quickly washed with cyclohexane to remove any aminodiphenylamine precipitated on the surface of the reservoir. The product is then dried in oven at about 40° C.

The reservoirs encapsulated with aminodiphenylamine are mixed with polymethacrylic prepolymer in a ratio of 1:50 for use as adhesive. Such mixture is applied to a screw such that as screw is tightened, the reservoirs break and release the curing agent that immediately cures the adhesives polymer locking the screw immediately in bolt, eliminating the need of taping or locking agent.

Example 6.2: POT Reservoirs Encapsulated with Mercaptobenzothiazole Corrosion Inhibitor The preparation procedure for preparing POT encapsulated MBT corrosion inhibitor is discussed in Example 2.1. A saturated solution of mercaptobenzothiazole (MBT) corrosion inhibitor was prepared by dissolving 2 g MBT in 100 ml ethanol. Poly-o-toluidine (POT) reservoirs, 2 g, were dispersed in this MBT/ethanol solution with stirring. Because the reservoirs are hollow with one or more openings on their surface, MBT and ethanol seeped into the interior of the hollow reservoirs. After 2 hours of stirring, ethanol was evaporated under vacuum with stirring at 60° C., such that the MBT was encapsulated inside the reservoir. After evaporating the ethanol, the POT reservoir/MBT product was quickly washed with ethanol to remove any corrosion inhibitor precipitated on the surface of the reservoir. The product was then dried in oven at 70° C.

The reservoirs encapsulated with MBT is added as additive to the adhesive formulation to inhibit corrosion. The adhesive could be polyacrylate, polyurethane or epoxy based. This adhesive is useful for bonding alloys and other metals. For example, in automotive applications, inner and outer door panels, lift gate panels, hoods and deck lids can be made of any combination of steel panels, aluminum panels, magnesium panels, carbon composite panels, or SMC panels to satisfy structural, weight, and appearance requirements and these adhesive could be used in bonding these metals and alloys.

VII. Biocide Additives

Example 7.1: POT Reservoirs Encapsulated with Isothiazolinones Biocide

Biocides belonging to the group of isothiazolinones are very effective. One such biocide is 2-methyl-4-isothiazolin-3-one (MITZ). In this example, a saturated solution of MITZ biocide is prepared by dissolving 2 g MITZ in 100 ml ethanol. Poly-o-toluidine (POT) reservoirs, 2 g, are dispersed in the MITZ/ethanol solution with stirring. Because the reservoirs are hollow with one or more openings on their surface, MITZ and ethanol seep inside the partially-open, hollow reservoirs. After 2 hours of stirring, ethanol is evaporated under vacuum with stirring at 60° C., such that the MITZ is encapsulated inside the reservoir. After evaporating the ethanol, the POT reservoir/MITZ product is quickly washed with ethanol to remove any MITZ precipitated on the surface of the reservoir. The product is then dried in oven at 40° C.

The reservoirs encapsulated with biocide are added as an additive to the coatings, adhesives, or chemicals, that desire biocidal properties. The coatings in this example could be both solvent and water based acrylic, epoxy, polyurethane, siloxane, polyurea, aspartic and their mixture, the adhesives could be acrylic, epoxy and polyurethane based or chemicals, both aqueous and solvent based, containing POHR encapsulated with biocide dispersed using dispersing agent.

VIII. Pesticide Additives

Example 8.1: POT Reservoirs Encapsulated with Thiamethoxam Pesticide

A saturated solution of thiamethoxam insecticide is prepared by dissolving 2 g thiamethoxam in 100 ml ethanol. Poly-o-toluidine (POT) reservoirs, 2 g, are dispersed in this thiamethoxam/ethanol solution with stirring. Because the reservoirs are hollow with one or more openings on their surface, thiamethoxam and ethanol seep inside the hollow reservoirs. After 2 hours of stirring, ethanol is evaporated under vacuum with stirring at 60° C., such that the thiamethoxam is encapsulated inside the reservoir. After evaporating the ethanol, the POT reservoir/MITZ product is quickly washed with ethanol to remove any thiamethoxam precipitated on the surface of the reservoir. The product is then dried in oven at 60° C.

Reservoirs encapsulated with pesticide is sprayed across the crop for their protection.

IX. Controlled Drug Release

Example 9.1: Poly-o-toluidine Reservoirs Encapsulated with Silver Sulfadiazine Drug In this example, silver sulfadiazine, a topical antibiotic used in wound dressing, is encapsulated in poly-o-toluidine POHR. Silver sulfadiazine (1 g) is dissolved in 100 ml water. Poly-o-toluidine reservoirs, 1 g are dispersed in aqueous silver sulfadiazine solution, with stirring. Because the reservoirs are hollow with one or more openings on their surface, silver sulfadiazine and water seep inside POHR. After two hours of stirring, water is evaporated under vacuum with stirring at 70° C. such that silver sulfadiazine is encapsulated inside the reservoir. The product is then quickly washed with water to remove any silver sulfadiazine precipitated on the surface on the reservoir. The product is then dried in oven at about 40° C.

Example 9.1.1. Drug Delivery in Response to Local Environment Change

The micro-reservoirs are dispersed into a wound dressing matrix such as polyethylene glycol based hydrogel. When the wound is infected, the pH in the vicinity of the wound increases that activates the micro-reservoirs to release the silver sulfadiazine directly onto wound.

Example 9.1.2 Drug Delivery in Response to External Trigger

A band-aid with microfabricated electrodes serving as cathode and anode and a hydrogel acting as electrolyte is assembled. POT reservoirs encapsulated with silver sulfadiazine is coated on cathode. Applying a DC voltage between the electrodes results in reduction of micro-reservoirs containing silver sulfadiazine resulting in release of Silver sulfadiazine from capsules. This is beneficial in timed release of silver sulfadiazine onto the wound dressing.

X. Fertilizer Additive

Example 10.1: Poly-o-toluidine Reservoirs Encapsulated with Urea Fertilizer

A solution of urea is prepared by dissolving 10 g Urea in 100 ml water. Poly-o-toluidine (POT) reservoirs, 10 g, are dispersed in this urea/water solution with stirring. Because the reservoirs are hollow with one or more openings on their surface, urea and water seep inside the hollow reservoirs. After 2 hours of stirring, water is evaporated under vacuum with stirring at 90° C., such that the urea is encapsulated inside the reservoir. After evaporating the water, the POT-POHR reservoir/urea product is quickly washed with water to remove any urea precipitated on the surface of the POT-POHR. The product is then dried in oven at about 60° C.

POHR encapsulated with urea are added to the soil to supply nutrients to plants over time.

XI. Corrosion Detection

Example 11.1: Poly-o-toluidine POHR Encapsulated with Phenolphthalein Dye Molecule Poly-o-toluidine (POT) partially-open, hollow reservoirs encapsulated with dye molecules are added into coatings that release dye molecules upon oxidation, that is corrosion of metal, thereby acting as a corrosion sensor that that can be detected visually or through a signal A solution of phenolphthalein is prepared by dissolving 0.5 g of phenolphthalein in 100 ml of ethanol. Poly-o-toluidine (POT) reservoirs, 2 g, are dispersed in this phenolphthalein/ethanol solution with stirring. Because the reservoirs are hollow with one or more openings on their surface, phenolphthalein and ethanol seep inside the hollow reservoirs. After 2 hours of stirring, ethanol is evaporated under vacuum with stirring at 60° C., such that the phenolphthalein is encapsulated inside the POHR. After evaporating the Ethanol, the POT reservoir/phenolphthalein product is quickly washed with ethanol to remove any phenolphthalein precipitated on the surface of the reservoir. The product is then dried in oven at 40° C.

The reservoirs encapsulated with phenolphthalein is added as additive to acrylic or epoxy based coatings. If there is a corrosion event occurring on the surface of the metal, the capsules will release phenolphthalein, thus a color change on the surface of coating will indicate corrosion.

What is claimed:

1. A plurality of partially-open, hollow reservoirs comprising at least one encapsulant;
a polymer comprising at least one conducting polymer;
wherein the plurality of partially-open, hollow reservoirs have at least one opening on their surface, such that the average opening area, in the aggregate, of said plurality of partially-open, hollow reservoirs is from about 0.25% to about 50% of the surface area in the aggregate of said plurality of partially-open, hollow reservoirs;
wherein the average size of said plurality of partially-open, hollow reservoirs is in the range of from about 200 nm to about 10,000 nm;
wherein said at least one encapsulant releasably resides within said plurality of partially-open, hollow reservoirs.

2. The plurality of partially-open, hollow reservoirs as recited in claim 1, wherein said at least one conducting polymer is selected from polyaniline-based polymer, polyaniline-based polymer derivatives, polypyrrole, polypyrrole based polymer, polypyrrole based polymer's derivatives, blends thereof, and mixtures thereof.

3. The plurality of partially-open, hollow reservoirs as recited in claim 2, wherein said conducting polymer is the polyaniline-based polymer, comprising at least one of polyaniline, poly-o-toluidine, poly-o-methoxyaniline, poly-o-ethylaniline, and poly-2-ethoxyaniline.

4. The plurality of partially-open, hollow reservoirs as recited in claim 3, wherein the plurality of partially-open, hollow reservoirs comprises the at least one polyaniline-based polymer in its base form, in its salt form, or in a blend of its base form and its salt form.

5. The plurality of partially-open, hollow reservoirs, as recited in claim 4, wherein the at least one polyaniline-based polymer is in its emeraldine form, in its leucoemeraldine form, or in its pernigraniline form, or a combination thereof.

6. The plurality of partially-open, hollow reservoirs as recited in claim 1, wherein said encapsulant is selected from the group consisting of a corrosion inhibiting additive, a lubricant additive, an adhesive additive, a biocide additive, an antifouling additive, a pesticide additive, a drug delivery additive, a corrosion sensor additive, a fragrance releasing additive, a catalyst additive, an ink additive, a dye additive, an enzyme additive, a reactant additive, and combinations thereof.

7. The plurality of partially-open, hollow reservoirs as recited in claim 6, wherein said corrosion inhibiting additive is selected from (a) an organic compound containing an amino group or carboxy group or salts of carboxylic acids, organic sulfides, heterocyclic rings, substituted aromatic rings, organic phosphates and phosphonic acids, quaternary ammonium compounds, imidazolines, aldehydes, sulfoxides, carboxylic acids, mercaptocarboxylic acids, imidazoles, oximes, azoles, tannins, substituted phenols, quinoline and quinolone compounds, substituted quinolines and quinalizarin, pyridinium group, pyrazine group, an azole derivative, and, one or more schiffs bases; (b) an organic compound containing one or more anions selected from the group comprising polyphosphate and its derivatives, nitrite, silicate, molybdate, and polymolybdate and its derivatives, vanadate and polyvanadate and its derivatives; and (c) an organic or inorganic compound comprising one or more cations selected from the group comprising lanthanides, magnesium, calcium, titanium, zirconium, yttrium, chromium and silver; combinations of components within each corrosion inhibiting additive group (a), (b), and (c); and combinations between one or more components of each additive group (a), (b), and (c).

8. The plurality of partially-open, hollow reservoirs as recited in claim 6, wherein said encapsulant is a lubricant additive selected from: (i) antioxidant additives selected from phenols and its derivatives, aromatic and aryl amines; (ii) anti-wear additives selected from metal alkyltiophosphate; (iii) dispersants selected from of phenates, sulfurized phenates, salicylates, naphthenates, stearates, carbamates, thiocarbamates, phosphorus derivatives; combinations of components within each lubricant additive group (i), (ii), and (iii); and combinations between one or more components of each lubricant additive group (i), (ii), and (iii).

9. The plurality of partially-open, hollow reservoirs as recited in claim 6, wherein said encapsulant is an adhesive additive selected from the following corrosion inhibitor encapsulants: chromate compositions, phosphates, silicates, nitrates, benzoates, mercaptobenzothiazoles, sodium molybdate formulations, phosphonic acids combined with amines, and combinations thereof.

10. A matrix comprising the plurality of partially-open, hollow reservoirs as recited in claim 6.

11. The plurality of partially-open, hollow reservoirs as recited in claim 1, wherein said partially-open, hollow reservoirs are nominally spherical-shaped hollow reservoirs, nominally rod-shaped hollow reservoirs, irregular-shaped hollow reservoirs, or a hollow micro-particles with more than one opening.

12. A process for preparing the plurality of the partially-open, hollow reservoirs as recited in claim 3, devoid of any encapsulant, wherein said conducting polymer is the polyaniline-based polymer, comprising the step of polymerizing a monomer of the polyaniline-based polymer by aqueous oxidative polymerization.

13. A process for preparing the plurality of partially-open, hollow reservoirs as recited in claim 1; comprising the steps of:
  (A1) preparing a plurality of partially-open, hollow reservoirs devoid of any encapsulant; and
  (A2) encapsulating the at least one encapsulant by (a) solvent evaporation; or (b) precipitation method; OR
comprising the step of:
  (BI) in-situ encapsulation of encapsulant during the polymerization process of partially-open, hollow reservoirs.

14. The process as recited in claim 13, wherein said conducting polymer is at least one polyaniline-based polymer.

15. The process as recited in claim 14, wherein said at least one polyaniline-based polymer is in its base form, or in its salt form, or in a blend of its base form and its salt form.

16. The process as recited in claim 15, wherein said at least one polyaniline-based polymer is in its emeraldine form or its leucoemeraldine form or pernigraniline form.

17. The process as recited in claim 13, wherein said encapsulant is selected from the group consisting of a corrosion inhibiting additive, a lubricant additive, an adhesive additive, a biocide additive, an antifouling additive, a pesticide additive, a drug delivery additive, a corrosion sensor additive, a fragrance releasing additive, a catalyst additive, an ink additive, a dye additive, an enzyme additive, a reactant additive, and combinations thereof.

18. A process for preparing a matrix comprising the plurality of partially-open, hollow reservoirs as recited in claim 1, comprising the steps of:
  (1) contacting said POHR with said matrix, and optionally
  (2) mixing said POHR in said matrix.

19. The process as recited in claim 18, wherein said matrix is a paint or a coating, and said encapsulant is a corrosion inhibitor.

20. A process for preparing the plurality of partially-open, hollow reservoirs as re-cited in claim 1, comprising the step of in-situ encapsulation of the at least one encapsulant inside the plurality of the partially-open, hollow reservoirs during synthesis of said plurality of the partially-open hollow reservoirs.

21. A process for releasing the at least one encapsulant from the plurality of the partially-open, hollow reservoirs as recited in claim 1, comprising the step of providing external stimuli to the plurality of the partially-open, hollow reservoirs; wherein the external stimuli is at least one of the following:

(1) changing the pH of the environment of the plurality of the partially-open, hollow reservoirs;
(2) changing the redox potential of the plurality of the partially-open, hollow reservoirs;
(3) changing the oxidation state of the plurality of the partially-open, hollow reservoirs;
(4) mechanically damaging the plurality of the partially-open, hollow reservoirs;
(5) changing the voltage applied to the plurality of the partially-open, hollow reservoirs; and
(6) changing the electrochemical potential of the plurality of the partially-open, hollow reservoirs.

22. A process for inhibiting corrosion in metal, comprising the step of coating said metal with a coating matrix comprising the partially-open, hollow reservoirs as recited in claim 1, wherein said at least one encapsulant comprises at least one corrosion inhibitor.

23. The process as recited in claim 22, wherein said at least one corrosion inhibitor is selected from (a) an organic compound containing an amino group or carboxy group or salts of carboxylic acids, organic sulfides, heterocyclic rings, substituted aromatic rings, organic phosphates and phosphonic acids, quaternary ammonium compounds, imidazolines, aldehydes, sulfoxides, carboxylic acids, mercaptocarboxylic acids, imidazoles, oximes, azoles, tannins, substituted phenols, quinoline and quinolone compounds, substituted quinolines and quinalizarin, pyridinium group, pyrazine group, an azole derivative, and, one or more schiffs bases; (b) an organic com-pound containing one or more anions selected from the group comprising polyphosphate and its derivatives, nitrite, silicate, molybdate, and polymolybdate and its derivatives, vanadate and poly-vanadate and its derivatives; and (c) an organic or inorganic compound comprising one or more cations selected from the group comprising lanthanides, magnesium, calcium, titanium, zirconium, yttrium, chromium and silver; combinations of components within each corrosion inhibiting additive group (a), (b), and (c); and combinations between one or more components of each additive group (a), (b), and (c).

24. The process as recited in claim 22, wherein the matrix coating is latexes, amino resins, polyurethanes, epoxies, phenolic resins, acrylic resins, polyester resins, alkyd resins, polysulfide resins, polyaspartic, polyurea, polylactones, adducts of amines, polyimide, polycarbonate, polyvinyl and halogenated polymer resins.

25. The process as recited in claim 22, wherein said metal is part of an automotive, a refinish part, a marine vehicle part, a part of an equipment, a metal cladding part, a part of any other vehicle, a part for any other vehicle, a part of a flying object, part of a decorative piece, industrial machinery, industrial machinery parts, pipe parts, tank parts, and bridge parts, coils, architecture and architecture parts, metal equipment and structures used in the power sector, metal equipment and structures used in the energy sector, and metal equipment and structures used in transportation sectors.

26. The process as recited in claim 18, wherein said matrix is a lubricant and said encapsulant is a lubricant additive selected from: (i) antioxidant additives selected from phenols and its derivatives, aromatic and aryl amines; (ii) anti-wear additives selected from metal alkyltiophosphate; (iii) dispersants selected from of phenates, sulfurized phenates, salicylates, naphthenates, stearates, carbamates, thiocarbamates, phosphorus derivatives; combinations of components within each lubricant additive group (i), (ii), and (iii); and combinations between one or more components of each lubricant additive group (i), (ii), and (iii).

27. The process as recited in claim 18, wherein said matrix is an adhesive, wherein said encapsulant is an adhesive additive selected from the following corrosion inhibitor encapsulants:
chromate compositions, phosphates, silicates, nitrates, benzoates, mercaptobenzothiazoles, sodium molybdate formulations, phosphonic acids combined with amines, and combinations thereof.

* * * * *